United States Patent
Furst et al.

(10) Patent No.: US 10,316,354 B2
(45) Date of Patent: Jun. 11, 2019

(54) ELECTROCHEMICAL SUBSTRATE PATTERNING AND ANALYTE DETECTION ON A TWO-ELECTRODE PLATFORM

(71) Applicant: CALIFORNIA INSTITUTE OF TECHNOLOGY, Pasadena, CA (US)

(72) Inventors: Ariel L. Furst, Pasadena, CA (US); Michael G. Hill, Pasadena, CA (US); Natalie B. Muren, Pasadena, CA (US); Jacqueline K. Barton, San Marino, CA (US)

(73) Assignee: California Institute of Technology, Pasadena, CA (US)

( * ) Notice: Subject to any disclaimer, the term of this patent is extended or adjusted under 35 U.S.C. 154(b) by 975 days.

(21) Appl. No.: 14/331,221

(22) Filed: Jul. 14, 2014

(65) Prior Publication Data
US 2015/0018232 A1 Jan. 15, 2015

Related U.S. Application Data

(60) Provisional application No. 61/845,822, filed on Jul. 12, 2013.

(51) Int. Cl.
*G01N 27/327* (2006.01)
*C40B 60/00* (2006.01)
*C12Q 1/6825* (2018.01)
*C12Q 1/68* (2018.01)

(52) U.S. Cl.
CPC .................. *C12Q 1/6825* (2013.01)

(58) Field of Classification Search
CPC ............... G01N 27/327; C12Q 1/68
USPC .......................................... 506/9
See application file for complete search history.

(56) References Cited

U.S. PATENT DOCUMENTS

2011/0210017 A1* 9/2011 Lai ..................... C07D 249/04
205/792

OTHER PUBLICATIONS

Das et al., An Ultrasensitive Universal Detector Based on Neutralizer Displacement, Nature Chemistry, 2012, 4, 642-648.*
Slinker et al., Multiplexed DNA-Modified Electrodes, J. Amer. Chem. Soc., 2010, 132, 2769-2774.*
Gorodetsky et al., DNA-Mediated Electrochemistry, Bioconjugate Chemistry, 2008, 19(12), 2285-2296.*
Devaraj et al., Chemoselective Covalent Coupling of Oligonucleotide Probes to Self-Assembled Monolayers, J. Amer. Chem. Soc., 2005, 127, 8600-8601.*
Park et al., Array-Based Electrical Detection of DNA with Nanoparticle Probes, Science, 2002, 295, 1503-1506. (Year: 2002).*
Furst, A., DNA-Mediated Charge Transport Devices for Protein Detection, Thesis, California Institute of Technology, 2015, 1-332. (Year: 2015).*
Gorodetsky et al., Scanning Electrochemical Microscopy of DNA Monolayers Modified with Nile Blue, Langmuir, 2008, 24, 14282-14288. (Year: 2008).*
Ahammad, A. J. Saleh; "Hydrogen Peroxide Biosensors Based on Horseradish Peroxidase and Hemoglobin"; Biosensors & Bioelectronics; 2013; pp. 1-11.
Bard, Allen J. et al.; "Scanning Electrochemical Microscopy. Introduction and Principles"; Anal. Chem.; 1989; 61; pp. 132-138.
Bard, Allen J. et al.; "Scanning Electrochemical Microscopy: Theory and Application of the Transient (Chronoamperometric) SECM Response"; Anal. Chem.; 1991; 63; pp. 1282-1288.
Baylin, Stephen B.; "DNA Methylation—Tying It All Together: Epigenetics, Genetics, Cell Cycle, and Cancer"; Science; vol. 277; Sep. 26, 1997; pp. 1948-1949.
Boon, Elizabeth M. et al.; "Mutation detection by electrocatalysis at DNA-modified electrodes"; Nature Biotechnology; vol. 18; Oct. 2000; pp. 1096-1100.
Boon, Elizabeth M. et al.; "An electrical probe of protein-DNA interactions on DNA-modified surfaces"; Nature Biotechnology; vol. 20; Mar. 2002; pp. 282-286.
Chaubey, Asha et al.; "Mediated biosensors"; Biosensors & Bioelectronics; 17; 2002; pp. 441-456.
Das, Jagotamoy et al.; "An ultrasensitive universal detector based on neutralizer displacement"; Nature Chemistry; vol. 4; Aug. 2012; pp. 642-648.
Furst, Ariel L. et al.; "DNA-Modified Electrodes Fabricated Using Copper-Free Click Chemistry for Enhanced Protein Detection"; Langmuir; 2013; 29; pp. 16141-16149.
Gorodetsky, Alon A. et al.; "Electrical Detection of TATA Binding Protein at DNA-Modified Microelectrodes"; J. Am. Chem. Soc. 2008; 130; pp. 2924-2925.
Gorodetsky, Alon A. et al.; "DNA-Mediated Electrochemistry"; Bioconjugate Chemistry; Dec. 2008; vol. 19, No. 12; pp. 2285-2296.
Goss, Charles A. et al.; "Application of (3-Mercaptopropyl)trimethoxysliane as a Molecular Adhesive in the Fabrication of Vapor-Deposited Gold Electrodes on Glass Substrates"; Analytical Chemistry; vol. 63; No. 1; Jan. 1, 1991; pp. 85-88.
Heyn, Holger et al.; "DNA methylation profiling in the clinic: applications and challenges"; Nature Reviews; Genetics; vol. 13; Oct. 2012; pp. 679-692.
Huang, ,Tian-Lung et al.; "Direct electrochemistry and biosensing of hydrogen peroxide of horseradish peroxidase immobilized at multiwalled carbon nanotube/alumina-coated silica nanocomposite modified glassy carbon electrode"; Sensors and Actuators B; 140; 2009; pp. 267-272.

(Continued)

*Primary Examiner* — Amy M Bunker
(74) *Attorney, Agent, or Firm* — Lewis Roca Rothgerber Christie LLP

(57) ABSTRACT

A two-electrode detection system having target substrates including nucleic acids, proteins, and/or small molecules on specifically defined regions of a single surface. The spatial distribution of the target substrate on the surface allows for more accurate substrate interactions and analysis. Additionally, the detection system of the present invention allows for patterning of different target substrates, thereby affording more accurate analysis of multiple substrate targets.

**13 Claims, 20 Drawing Sheets
(11 of 20 Drawing Sheet(s) Filed in Color)
Specification includes a Sequence Listing.**

(56) References Cited

OTHER PUBLICATIONS

Jones, Peter A. et al.; "The Fundamental Role of Epigenetic Events in Cancer"; Nature Reviews; Genetics; vol. 3; Jun. 2002; pp. 415-428.

Jones, Peter A. et al.; "Cancer epigenetics comes of age"; Nature Genetics; vol. 21; Feb. 1999; pp. 163-167.

Kelley, Shana O. et al.; "Single-base mismatch detection based on charge transduction through DNA"; Nucleic Acids Research; 1999; vol. 27; No. 24; pp. 4830-4837.

Lei, Cun-Xi et al.; "An amperometric hydrogen peroxide biosensor based on immobilizing horseradish peroxidase to a nano-Au monolayer supported by sol-gel derived carbon ceramic electrode"; Bioelecrrochemistry 65; 2004; pp. 33-39.

Lei, Cun-Xi et al.; "Immobilization of Enzymes on the Nano-Au Film Modified Glassy Carbon Electrode for the Determination of Hydrogen Peroxide and Glucose"; Electroanalysis; 2004; 16, No. 9; pp. 736-740.

Lei, Cun-Xi et al.; "An $H_2O_2$ Biosensor Based on Immobilization of Horseradish Peroxidase Labeled Nano-Au in Silica Sol-Gel/Alginate Composite Film"; Analytical Letters; 38; 2005; pp. 1721-1734.

Li, Chun-Xiang et al.; "Amperometric Hydrogen Peroxide Biosensor Based on Horseradish Peroxidase-labeled Nano-Au Colloids Immobilized on Poly(2,6-pyridinedicarboxylic acid) Layer by Cysteamine"; Analytical Sciences; Sep. 2004; vol. 20; pp. 1277-1281.

Muren, Natalie B. et al.; "Solution, surface, and single molecule platforms for the study of DNA-mediated charge transport"; Phys. Chem. Chem. Phys.; 2012; 14; pp. 13754-13771.

Nikolov, Dimitar B. et al.; "Crystal structure of TFIID TATA-box binding protein"; Nature; vol. 360; Nov. 5, 1992; pp. 40-46.

Pradhan, Sriharsa et al.; "Recombinant Human DNA (Cytosine-5) Methyltransferase: I. Expression, Purification, and Comparison of De Novo and Maintenance Methylation"; The Journal of Biological Chemistry; vol. 274; No. 46; Nov. 12, 1999; pp. 33002-33010.

Rostovtsev, Vsevolod V. et al.; "A Stepwise Huisgen Cycloaddition Process: Copper(I)-Catalyzed Regioselective "Ligation"of Azides and Terminal Alkynes"; Angew. Chem. Int. Ed.; 2002; 41; No. 14; pp. 2596-2599.

Smalley, John F. et al.; "The Kinetics of Electron Transfer through Ferrocene-Terminated Alkanethiol Monolayers on Gold"; J. Phys. Chem.; 1995; 99; pp. 13141-13149.

Takahashi, Shigehiro et al.; "Recent Progress in Ferrocene-Modified Thin Films and Nanoparticles for Biosensors"; Materials 2013; 6; pp. 5742-5762.

Tornoe, Christian W. et al.; "Peptidotriazoles on Solid Phase: [1,2,3]-Triazoles by Regiospecific Copper(I)-Catalyzed 1,3-Dipolar Cycloadditions of Terminal Alkynes to Azides"; J. Org. Chem. 2002; 67; pp. 3057-3064.

Wittstock, Gunther; "Imaging Localized Reactivities of Surfaces by Scanning Electrochemical Microscopy"; Solid-Liquid Interfaces; Topics Appl. Phys. 85; 2003; pp. 335-366.

Zoski, Cynthia G. et al.; "Scanning Electrochemical Microscopy. 57. SECM Tip Voltammetry at Different Substrate Potentials under Quasi-Steady-State and Steady-State Conditions"; Anal. Chem. 2007; 79; pp. 4957-4966.

\* cited by examiner

FIG. 2A
FIG. 2B
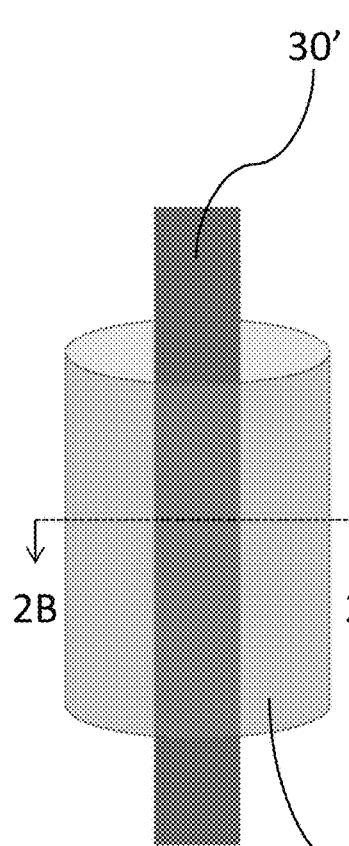
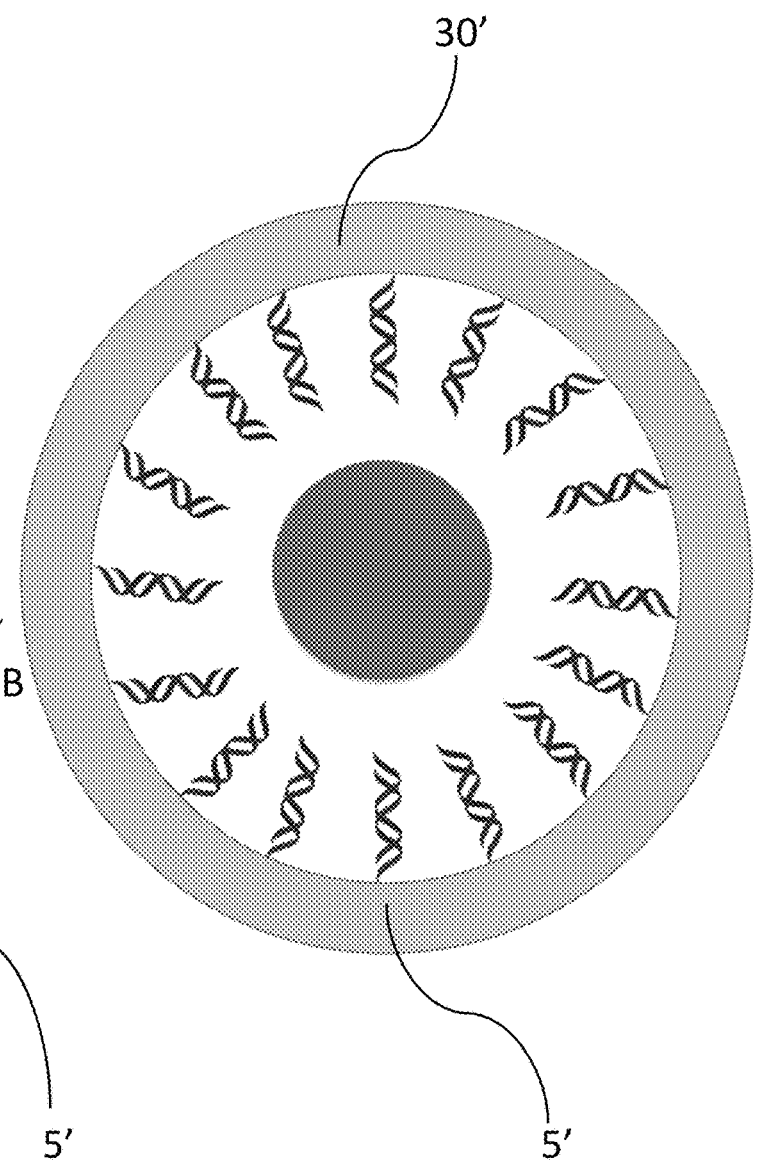

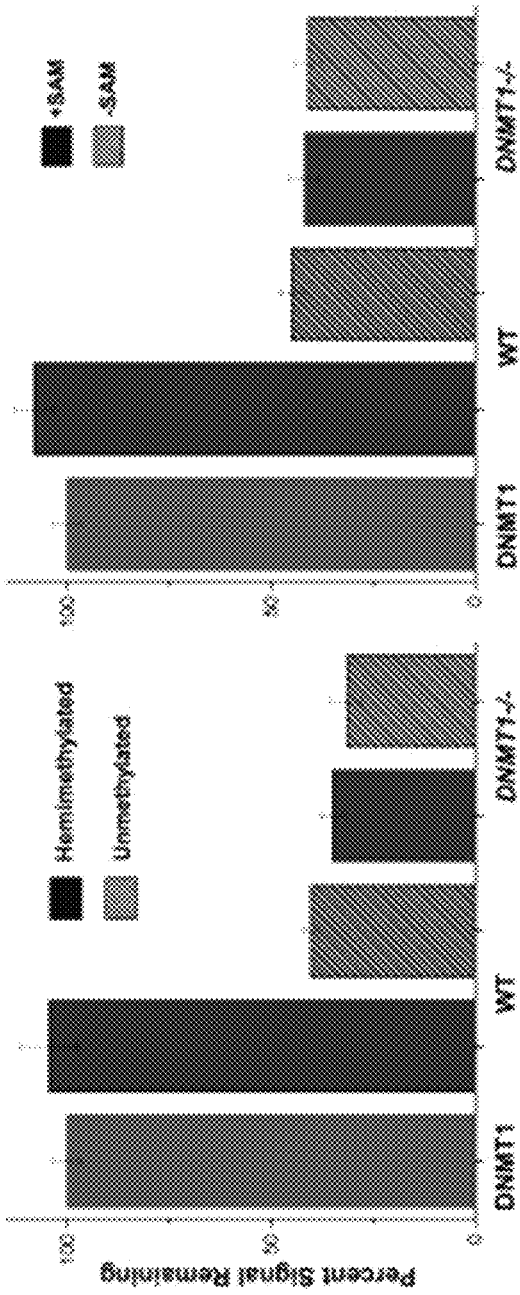

SEQUENCE LISTING

```
<160> NUMBER OF SEQ ID NOS: 6

<210> SEQ ID NO 1
<211> LENGTH: 17
<212> TYPE: DNA
<213> ORGANISM: artificial
<220> FEATURE:
<223> OTHER INFORMATION: Well Matched Oligo

<400> SEQUENCE: 1
gctcagtacg acgtcga                                                    17

<210> SEQ ID NO 2
<211> LENGTH: 17
<212> TYPE: DNA
<213> ORGANISM: artificial
<220> FEATURE:
<223> OTHER INFORMATION: Mismatch Oligo at 9th

<400> SEQUENCE: 2
tcgacgtcat actgagc                                                    17

<210> SEQ ID NO 3
<211> LENGTH: 22
<212> TYPE: DNA
<213> ORGANISM: artificial
<220> FEATURE:
<223> OTHER INFORMATION: TBP binding oligo

<400> SEQUENCE: 3
ggcgtctata aagcgatcgc ga                                              22

<210> SEQ ID NO 4
<211> LENGTH: 26
<212> TYPE: DNA
<213> ORGANISM: artificial
<220> FEATURE:
<223> OTHER INFORMATION: Alkyne with BssHII

<400> SEQUENCE: 4
gactgagtac tgcgcgcact gatagc                                          26

<210> SEQ ID NO 5
<211> LENGTH: 26
<212> TYPE: DNA
<213> ORGANISM: artificial
<220> FEATURE:
<223> OTHER INFORMATION: Complement with BssHII

<400> SEQUENCE: 5
gctatcagtg cgcgcagtac tcagtc                                          26

<210> SEQ ID NO 6
<211> LENGTH: 27
```

```
<212> TYPE: DNA
<213> ORGANISM: artificial
<220> FEATURE:
<223> OTHER INFORMATION: Methylated Complement with BssHII

<400> SEQUENCE: 6
gctatcagtg cgcmgcagta ctcagtc                                            27
```

ELECTROCHEMICAL SUBSTRATE PATTERNING AND ANALYTE DETECTION ON A TWO-ELECTRODE PLATFORM

CROSS-REFERENCE TO RELATED APPLICATION(S)

The present application claims priority to and the benefit of U.S. Provisional Application Ser. No. 61/845,822 filed on Jul. 12, 2013 the entire contents of which are incorporated herein by reference.

STATEMENT REGARDING FEDERALLY SPONSORED RESEARCH OR DEVELOPMENT

This invention was made with government support under GM061077 awarded by the National Institutes of Health. The government has certain rights in the invention.

INCORPORATION BY REFERENCE

The instant application contains a Sequence Listing which has been submitted in ASCII format via EFS-Web and is hereby incorporated by reference in its entirety. Said ASCII copy was created on Feb. 21, 2019, is named 75304SEQ-LISTING.txt, and is 1,400 bytes in size.

BACKGROUND

Detection of nucleic acids, proteins, and small molecules is helpful for complete patient analysis. For example, nucleic acid sensors are useful for the detection of many biological markers of disease, protein detection identifies a host response, and small molecule detection profiles metabolites. Although fluorescence-based nucleic acid hybridization arrays have proven useful for high-throughput screening applications, they have not shown utility for bench-top clinical diagnostics. Electrochemical assays based on charge are well suited for point-of-care applications mostly because charge detection requires only simple electrode instrumentation and does not require stringent procedures to report on mutations, protein binding, as well as other perturbations.

In conventional analytical platforms, electrochemical readout occurs at the surface onto which the substrate monolayers are assembled. As a result, these conventional assays report on bulk changes that occur over the entire electrode area. Multiplexing has enabled multiple experimental conditions to be run in parallel, however, these multiplex platforms still yield only average changes that occur over the entire surface. Comparing individual electrodes can be misleading, as small variations can lead to substantial differences in electrochemical responses.

Electrochemical methods are low cost, portable, and require only modest instrumentation. Electrochemistry has been used to detect nucleic acids with high sensitivity and without the need for polymerase amplification, however facile analysis and detection of multiple substrates in the presence of protein analytes has remained challenging.

SUMMARY

Aspects of the invention are directed to a two-electrode detection system and method of analyzing target substrates using the detection system.

In some embodiments of the present invention, a detection system includes at least one target substrate including a nucleic acid, protein and/or small molecule, the detection system, includes: a substrate surface (10) comprising a first electrode (5); a substrate surface linker (15) having a first moiety (16) capable of attaching to the substrate surface (10) and a second moiety (18) capable of attaching to the at least one target substrate (20); the at least one target substrate (20) having a linker moiety (21) capable of attaching to the second moiety (18) of the substrate surface linker (15); an inactive catalyst precursor (19a); reactants selected to undergo a redox reaction (25) mediated by the at least one target substrate; and at least one second electrode (30) facing the first electrode (5) with the at least one target substrate being between the first and second electrodes.

In some embodiments of the present invention, the detection system more specifically includes a second moiety (18) of the substrate surface linker that includes an azide or an alkyne, wherein the linker moiety of the at least one target substrate has an azide or an alkyne (21), wherein the inactive catalyst precursor comprises copper (II) (19a), and wherein the second moiety (18) of the substrate surface linker (15) covalently binds to the linker moiety (21) of the at least one target substrate (20) upon application of a negative potential.

In some embodiments of the present invention, the detection system also includes a passivating compound having a first moiety (36) capable of attaching to the substrate surface and a second moiety (38) for passivation.

In some embodiments of the present invention, the detection system more specifically includes more than one type of target substrate (20), wherein the at least one second electrode (30) includes more than one second electrode, and wherein each of the more than one type of target substrates (20) has a corresponding second electrode (30).

In some embodiments of the present invention, a method of analyzing at least one target substrate including nucleic acids, proteins and/or small molecules comprising using the detection system as described herein, the method including attaching the substrate surface linker to the substrate surface; adding the at least one target substrate to the substrate surface and an inactive precursor catalyst; applying a negative potential to the at least one second electrode to thereby activate the precursor catalyst and attach the at least first target substrate to the substrate surface linker; adding the reactants selected to undergo a redox reaction; applying a negative potential to the first electrode to induce the redox reaction; collecting a first set of electrochemical data of the redox reaction from the at least one second electrode; adding an analyte to the substrate surface; and collecting a second set of electrochemical data of the redox reaction.

BRIEF DESCRIPTION OF THE DRAWINGS

The patent or application file contains at least one drawing executed in color. Copies of this patent or patent application publication with color drawings will be provided by the Office upon request and payment of the necessary fee.

These and other features and advantages of the present invention will be better understood by reference to the following detailed description when considered in conjunction with the accompanying drawings.

FIG. 2A is schematic of a hollow cylindrical substrate electrode (5') with a rod second (probe) electrode (30'), according to embodiments of the present invention.

FIG. 2B is a cross section of FIG. 2A, taken along line 2B-2B, according to embodiments of the present invention.

FIG. 14A is a graph showing the percent signal remaining on hemimethylated (solid) and unmethylated (cross hatched) DNA, as indicated, with wild type lysate (blue) and DNMT1−/− lysate (red) compared to purified DNMT1 (green), according to embodiments of the present invention.

FIG. 14B is a graph showing the percent signal remaining in the presence of SAM (solid) or absence of SAM (cross hatched), as indicated, with wild type lysate (blue) and DNMT1−/− lysate (red) compared to purified DNMT1 (green), according to embodiments of the present invention.

DETAILED DESCRIPTION

Embodiments of the present invention are directed to a two-electrode detection system that allows for spatial resolution of target substrates including nucleic acids, proteins, and/or small molecules on specifically defined regions on a single surface. The spatial resolution of the target substrate is the result of passivating compounds together with target substrates on the substrate surface resulting in easily applied and well-spaced target substrates for more accurate analyte interactions and analysis. Additionally, the detection system of the present invention allows for patterning of different target substrates, thereby affording more accurate analysis of multiple targets.

The detection system according to embodiments of the present invention, utilizes a first electrode having a surface coated with target substrates. The coating of the target substrates onto the first electrode surface is controlled using a secondary electrode that catalyzes the covalent bonding of a target substrate to the substrate in the presence of an electrochemical catalyst. This mechanism allows for selective patterning of different types of target substrates onto one surface. Additionally, as described herein in more detail, applying a passivating compound to the electrode surface together with the target substrates, allows for the target substrates to be more spatially distributed on the substrate surface which thereby allows for more accurate analyte interactions and analysis. The detection system of the present invention provides a means for electrochemical analysis using a reduction-oxidation (redox) reaction. That is, as described herein in more detail, a redox reaction is mediating by an "unperturbed" target substrate providing a first set of electrochemical data, which may be "perturbed" in the presence of an analyte, thereby inhibiting the redox reaction and the resulting in a second set of electrochemical data.

Figure 1:
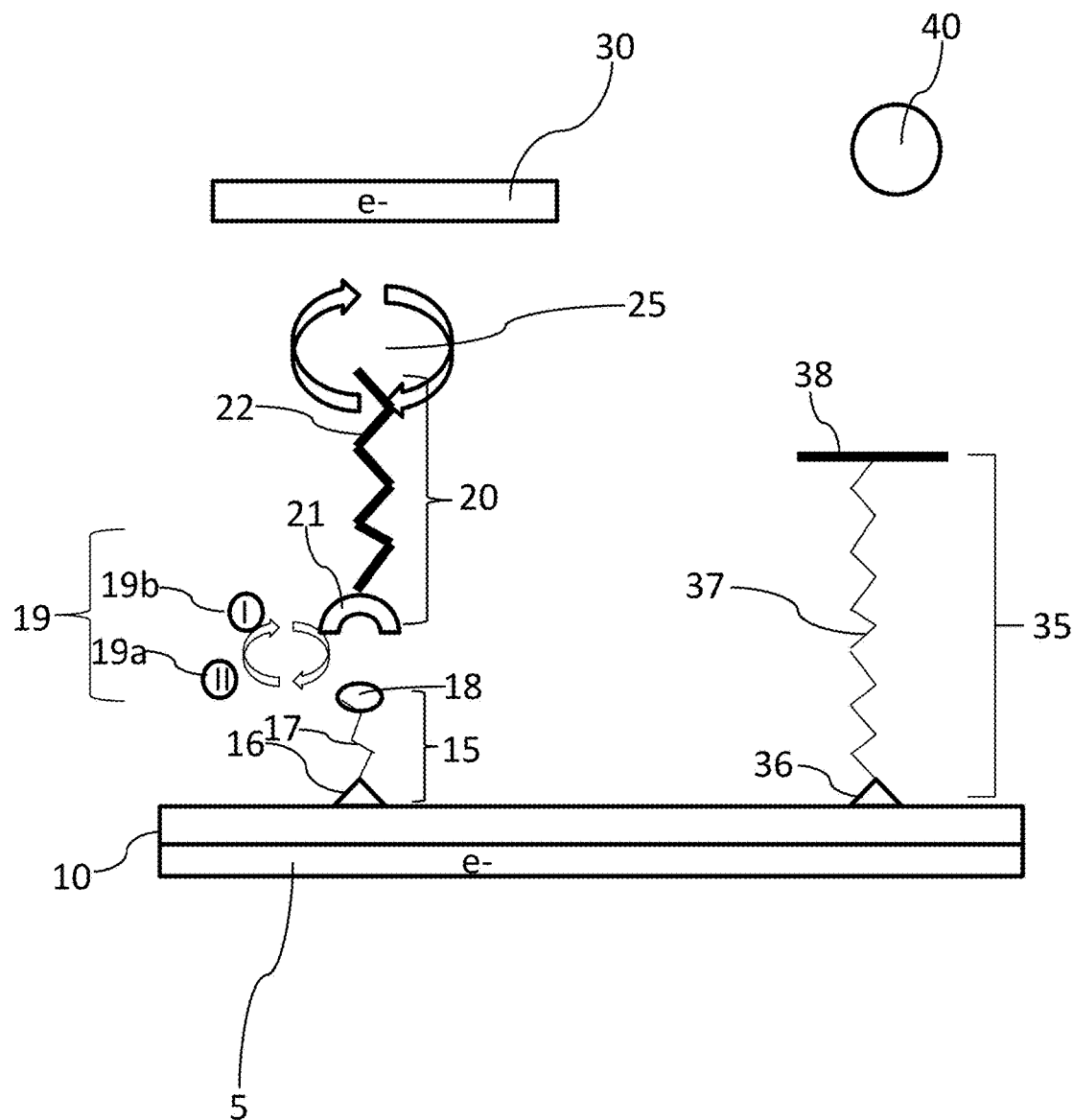
FIG. 1 is a schematic of the components of a detection system, according to embodiments of the present invention.
Figure 3:
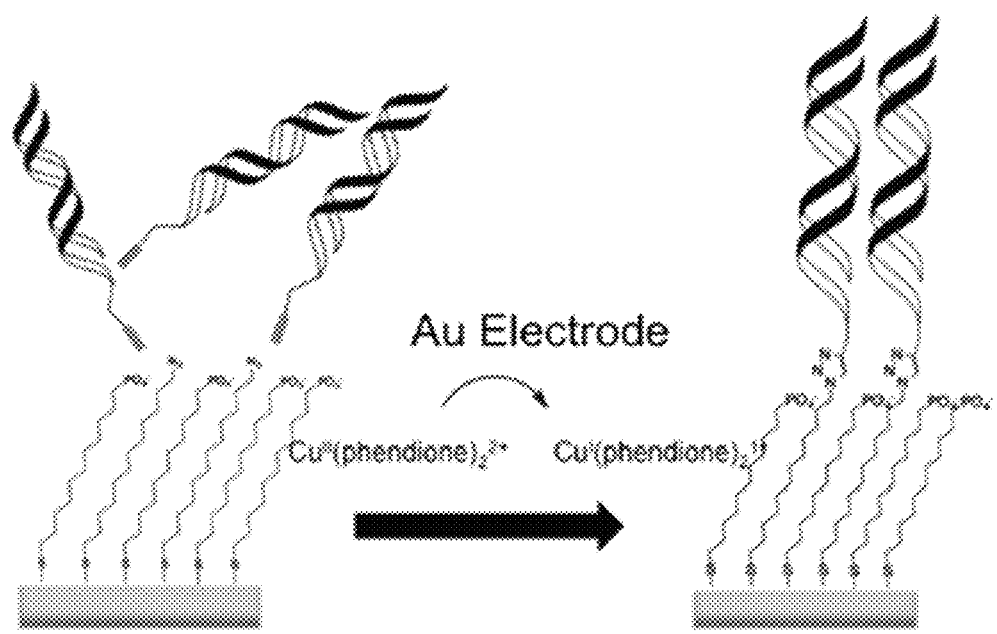
FIG. 3 is a schematic of a platform electrode with an inert copper II (Cu (II)) catalyst being electrochemically activated with a gold (Au) electrode to an active Cu(I) species capable of catalyzing the [3+2] azide-alkyne cycloaddition between alkyne-modified DNA and an azide terminated thiol monolayer, according to embodiments of the present invention.

The detection system is further described using the following terms with reference to FIG. 1. The schematic shapes shown in FIG. 1 do not represent any actual shapes of the referenced molecules and do not necessarily represent a particular molecule that may have that shape or be known to be represented with a particular shape.

As used herein, a target substrate (20) refers to nucleic acids, proteins and/or small molecules (22) that are immobilized on the substrate surface (10) of a substrate electrode (5). A target substrate (20) is a modified nucleic acid, protein, or small molecule (22) having a linker moiety (21) that is capable of attaching to the second moiety (18) of the substrate surface linker (15). In some embodiments, the target substrate forms a monolayer on the substrate surface. In some embodiments, more than one target substrate is immobilized on the substrate surface.

In some embodiments of the present invention, target substrates include any nucleic acid, protein, and/or small molecule that is capable of mediating charge transport. For example, deoxyribonucleic acid (DNA), horseradish peroxidase, hemoglobin, and ferrocene, each of which is disclosed herein or described previously in Ahammad, 2013, *J. Biosens Bioelectron., S:9*, 1-11; Das et al., 2012, *Nature Chem.*, 4, 642-648; and Smalley et al., 1995, *J. Phys. Chem.*, 99, 13141-13149, the entire contents of all of which are herein incorporated by reference.

As used herein, substrate surface (10) refers to the surface material that covers the surface electrode (5). A person having ordinary skill in the art would be able to select a suitable electrode and substrate surface from those known in the art. In some embodiments of the present invention, the substrate surface includes gold or carbon (e.g, glassy carbon). In some embodiments, gold is applied by evaporation to a glass slide electrode as described herein with reference to Goss et al., 1991, *Anal. Chem.*, 63, 85-88, the entire contents of which are herein incorporated by reference. In some embodiments, a gold electrode or rotating disk electrode (RDE) is used as described, for example, in Furst et al., 2013, *Langmuir*, 29, 16141-16149, the entire contents of which are herein incorporated by reference. Other gold-based as well as carbon-based substrate electrodes are well known and described in the art, for example, Lei et al., 2004, *Electroanalysis*, 16, 736-740; Lei et al., 2005, *Anal. Lett.*, 38, 1721-1734, Li et al., 2004, *Anal. Sci.*, 20, 1277-1281, Lei et al., 2004, *Biochemistry*, 65, 33-39, and Huang et al., 2009, *Sens. Actuators B. Chem.*, 140, 267-272, the entire contents of all of which are herein incorporated by reference. In some embodiments of the present invention, the two-electrode system utilizes scanning electrochemical microscopy (SECM). (See, e.g., Bard et al., 1989, *Anal. Chem.* 61, 132-138; Wittstock, G. Imaging Localized Reactivities of Surfaces by Scanning Electrochemical Microscopy. In *Solid-Liquid Interfaces (Topics in Applied Physics, Vol. 85)*; Wiley-VCH; Weinheim; 2003; 335-364; Bard et al., 1991, *Anal. Chem.* 63, 1282-1288; and Zoski et al., 2007, *Anal.*

*Chem.* 79, 4957-4966, the entire contents of all of which are herein incorporated by reference.)

As used herein, substrate surface linker (15) (also referred to herein as "substrate linker") refers to a compound having a chain moiety (17) providing an unreactive length, a first moiety (16) (i.e., a tail moiety) that is capable of attaching to the substrate surface, and a second moiety (i.e., a head moiety) (18) that is capable of attaching to the target substrate (20). In some embodiments of the present invention, the substrate linker first moiety (16) is a thiol or diazonium salt that is capable of attaching to the substrate surface (10). Thiol groups and diazonium salt groups are well known in the art for attachment to gold substrate surfaces, as described herein, and, for example, in Takahashi et al., 2013, *Materials,* 6, 5742-5762, the entire contents of which are herein incorporated by reference.

In some embodiments of the present invention, the substrate surface linker has a second "head" moiety (18) that is capable of binding to the linker moiety (21) of the target substrate (20). In some embodiments of the present invention, the second moiety (18) of the substrate surface linker (15) binds to the linker moiety (21) of the target substrate (20) via azide-alkyne coupling by a copper (Cu)-catalyst (19). This reaction utilizes an inactive catalyst precursor that includes copper (II) (Cu(II)) (19a) that is activated to Cu(I) (19b) by the negative potential of the second electrode (30) as described below. As such, the second moiety (18) of the substrate surface linker may be an azide or an alkyne which upon activation by the copper catalyst (19) binds to a corresponding azide or alkyne linker moiety group (21) on the target substrate (20). In some embodiments of the present invention, the second moiety (18) of the substrate surface linker (15) may be an azide and the linker moiety (21) of the target substrate (20) may be an alkyne. In other embodiments, the second moiety (18) of the substrate surface linker (15) may be an alkyne and the linker moiety (21) of the target substrate (20) may be an azide. In some embodiments, the azide for the second moiety (18) of the substrate surface linker or the linker moiety (21) of the target substrate may be a 6-carbon azide, a 9-carbon azide, or a 12-carbon azide. In some embodiments, the inactive catalytic precursor (19a) is $Cu(II)(bathophen)_2$ or $Cu(II)(phendione)_2$. Reactions for coupling an azide or alkyne group to a linker compound or a target substrate are well known in the art, as described, for example, in Rostovtsev et al., *Angew. Chem.—Int. Edit.* 2002, 41, 2596, and Tomoe et al., *J. Org. Chem.* 2002, 67, 3057, the entire contents of both of which are incorporated herein by reference.

Using this copper catalyzed azide-alkyne coupling method, the patterning of different target substrates is possible because the attachment of a target substrate (20) to the substrate surface (10) through a substrate linker (15) is dependent upon the activation to Cu(I) by a second (probe) electrode (30). That is, the addition of a target substrate to a substrate coated with a linker compound, selectively attaches the target substrate at locations on the substrate surface (10) corresponding in position to the position of a second (probe) electrode (30) with an active charge potential. As such, after incubation of the substrate surface with a substrate surface linker and a first target substrate and activation of an inactive copper catalyst (19a) to an active copper catalyst (19b) at a selected first position, the excess first target substrate may be washed, followed by incubation with a second target substrate and inactive copper precursor (19a) in combination with actuation of a different second electrode at a selected second position of the substrate surface (10), which second position is different from the first position. This method may be repeated for multiple target substrates at multiple different positions of the substrate surface (10). In this way, it is possible for the substrate surface (10) of the detection system according to embodiments of the present invention to be patterned with multiple types of target substrates (20).

As used herein, redox reaction (25) refers to a reduction/oxidation reaction that is mediated by the target substrate (20) allowing for measurement of a change in current based on perturbations (e.g., binding, lack of binding, cleaving) to the target substrate (20). In some embodiments of the present invention, the measurement of the redox reaction is carried out by the second electrode (30) positioned facing (e.g., above) the redox reaction. The second electrode (30) may also be referred to as the "top electrode" or a "probe electrode" as it is above the first substrate electrode (5) with the target substrate (20) and redox reaction (25) therebetween. The redox reaction (25) is selected based on the target substrate (20).

As used herein, the term "above" and "below" and similar terms, are defined with reference to the drawings. However, as would be understood by those of ordinary skill in the art, as the orientation of the components depicted in the drawings changes, the "above" and "below" designations may also change, such that in some embodiments, "above" may actually be "below," and vice versa.

In some embodiments of the present invention, a DNA target substrate is coupled with a redox reaction that takes advantage of the DNA-mediated charge transport (DNA CT). In brief, DNA CT refers to the ability of DNA to conduct charge through its double helix, $\pi$ stack structure. The conduction of charge through DNA is sensitive to perturbations (e.g., binding, cleaving, or mismatched strands), which are easily detected in a redox reaction readout, as described herein, and, for example, in Kelley et al., 1999, *Nucleic Acids Res.,* 27, 4830-4837 and Boon et al., 2000, *Nat. Biotechnol.,* 18, 1096-1100, the entire contents of both of which are herein incorporated by reference. As described and shown in detail herein, through electrochemical currents from the substrate electrode, methylene blue (MB), which intercalates into DNA, is reduced to leucomethylene blue (LB), and LB dissociates from the DNA and reduces ferricyanide to ferrocyanide. (See Examples 1 and 2.)

In some embodiments of the present invention, a metalloprotein, e.g., hemoglobin, may be coupled with a dioxygen reaction to form peroxide, which is detected at the secondary electrode using horseradish peroxidase, as described, for example, in Ahammad, 2013 supra.

As used herein, passivating compound (35) refers to a chemical compound having a first moiety (36) that is capable of attaching to the substrate surface (10) and having a passivating (e.g., "blocking") moiety (38) that is unreactive with the adjacent target substrate. The passivating compound (35) may have a length (37) (e.g., a carbon chain) that is approximately as long as the combined length of the substrate linker (15) and the target substrate (20). In some embodiments of the present invention, the passivating compound (35) may be immobilized on the substrate surface (10) along with the target substrate (20) and substrate linker (15) in order to provide improved spatial resolution of the target substrates for more accurate interactions (e.g., binding, cleaving) at the target substrate in the presence or absence of an analyte (40).

In some embodiments of the present invention, the amount of target substrate relative to passivating compound may be 1% to 100%. For less dense monolayers of target substrate, the amount of target substrate relative to passivating compound may be about 1% to about 20%. With such a low distribution of target substrate, larger sterically bulky targets and/or analytes can be accurately analyzed. For densely patterned target substrates, the amount of target substrate relative to passivating compound may be up to 100%. At 100% targeting substrate, no passivating compound is used. Such a dense pattern of target substrate is possible with smaller targets and/or analytes.

In some embodiments of the present invention, the passivating compound (35) may be selected from alkanes, alcohols, carboxylic acids, phosphates, and combinations thereof. In some embodiments, the passivating compound may be selected from mercaptoethanol, mercaptohexanol, mercaptoundecanol, mercaptohexane, mercaptohexanoic acid, mercaptoundecanoic acid, mercaptoundecylphosphoric acid, and combinations thereof.

As used herein, the term analyte (40) and analyte sample are used interchangeably to refer to a group (or groups) of molecules that are being assayed for its (or their) effect or lack of effect on a target substrate. For example, the analyte (40) may be a nucleic acid, a protein, a small molecule, or a solution of nucleic acids, proteins and/or small molecules, a cell suspension, or a cell lysate that is added to the two-electrode detection system as disclosed herein having at least one target substrate.

In some embodiments of the present invention, the substrate electrode and second electrode may be oriented in any suitable configuration. For example, in addition to the sandwich configuration in which the substrate electrode (5) is on the bottom and the second probe electrode (30) is on the top as shown in FIG. 1, the substrate electrode may be a hollow cylindrical electrode (5') with a secondary rod electrode (30') inserted into the center of the cylinder as shown in FIGS. 2A and 2B.

The following Examples are presented for illustrative purposes only, and do not limit the scope or content of the present application.

EXAMPLES

Example 1

DNA Array Platform Using Click Chemistry. Some embodiments of the present invention are directed to a simplified, macroscopic scanning electrochemical microscopy (SECM)-like system for analyzing DNA arrays composed of different sequences grafted onto a single surface. The platform according to some embodiments of the present invention does not require specialized equipment, but instead requires a standard bipotentiostat, microelectrode, and an x,y,z-stage. An electrochemical readout is accomplished via amperometric detection at a probe electrode positioned above the substrate surface. As multiple DNA sequences are patterned onto the same surface, different sequences may be examined under identical conditions with redundancy and internal controls.

Figure 4A:
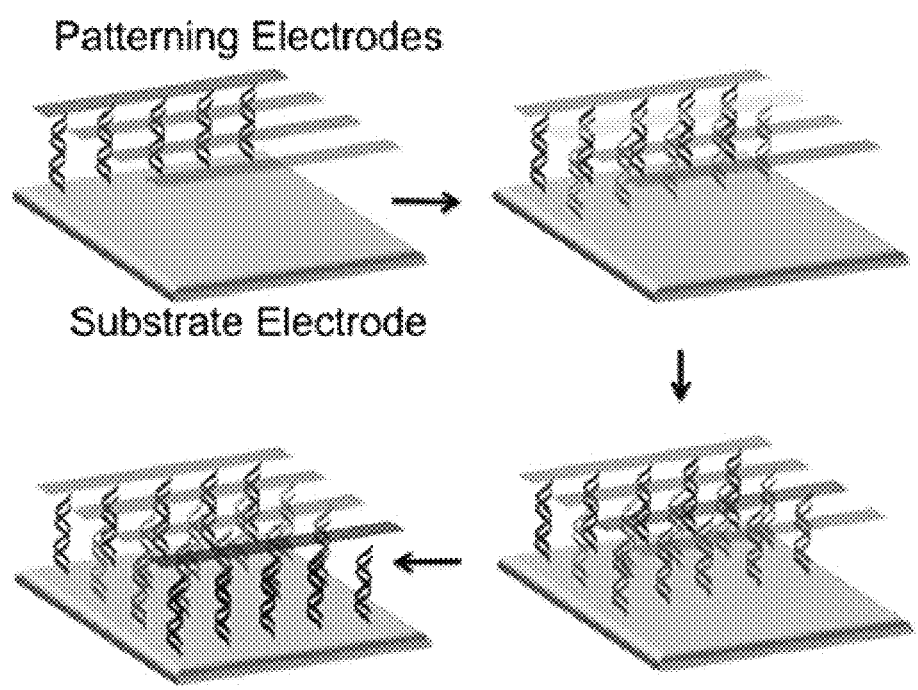
FIG. 4A is a schematic showing the patterning of four different sequences of DNA onto a single substrate pad through sequential catalyst activations, each different type of DNA is represented by a different color (red, yellow, green or blue), according to embodiments of the present invention.
Figure 4B:
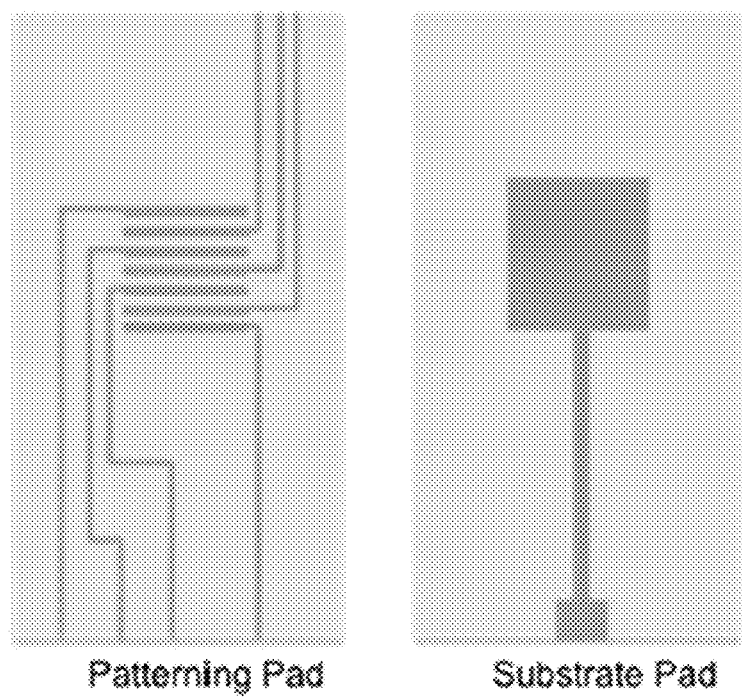
FIG. 4B is a schematic showing a design for patterning electrodes and a substrate electrode in which the patterning pad contains four working electrodes that are individually addressable interspersed with three reference electrodes, and the substrate pad contains a single, large gold pad and a working electrode contact to the pad, according to embodiments of the present invention.

A strategy for grafting DNA arrays is schematically shown in FIGS. 3, 4A, 4B, and 4C. Surfaces were prepared by vapor-depositing gold films onto glass microscope slides, forming both square substrate electrodes and a patterning electrode that features interdigitated patterning lines spaced 2-mm apart, as described herein (Materials and Methods). Next, mixed monolayers were self-assembled onto the substrate electrodes from an ethanolic solution of 12-azidododecane-1-thiol and 11-mercaptoundecylphosphoric acid, producing a passivated surface against ferricyanide and methylene blue, electrochemical reporters of DNA charge transport (CT). Duplex DNAs, as described herein (Materials and Methods), were then grafted onto the substrate electrodes by sandwiching an aqueous solution of [Cu(phendione)$_2$][SO$_4$] and an alkyne-labeled DNA sequence between the substrate and patterning pads separated by a thin (200 µm) Teflon spacer. Electrochemical reduction of Cu(phendione)$_2^{2+}$ at specific working electrodes on the patterning pad yields spatially isolated DNA duplexes covalently bound to the substrate via Cu(I)-catalyzed azide/alkyne coupling (FIG. 4A). Using this method, multiple DNA sequences may be grafted onto the same substrate by rinsing the surface following Cu(I) activation, then repeating the procedure with a different DNA sequence, as described herein (Materials and Methods). The electrochemical control of the copper catalyst from a secondary electrode offers a unique route to functionalize the surface with DNA under spatial control.

Figure 5A:
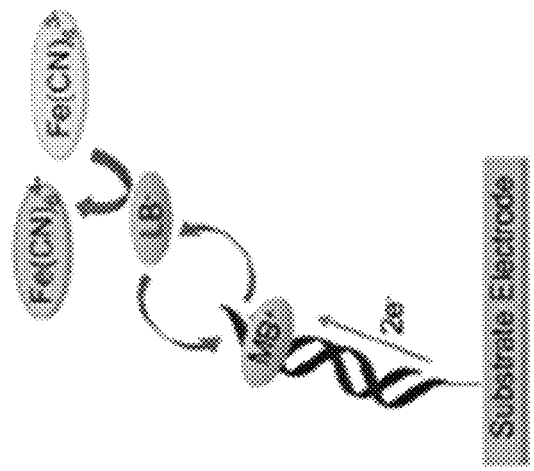
FIG. 5A is a schematic depicting conventional detection of electrocatalytic currents measured at the substrate electrode—in which intercalated methylene blue (MB) is reduced to leucomethylene blue (LB) through well matched DNA duplexes; LB dissociates from the duplex and reduces ferricyanide to ferrocyanide; and the resulting MB intercalates back into the DNA duplex to restart the cycle.
Figure 5B:
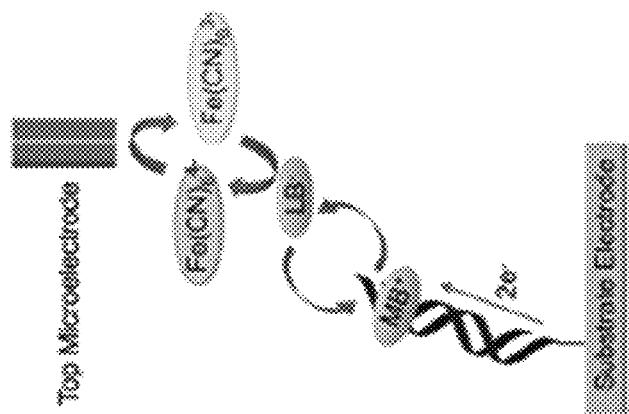
FIG. 5B is a schematic of two-electrode electrocatalysis in which the same chemistry occurs at the substrate electrode as depicted in FIG. 5A, except that a probe (top) microelectrode reduces the electrochemically-produced ferrocyanide back to ferricyanide, providing an amperometric readout via a secondary electrode, according to embodiments of the present invention.
Figure 6A:
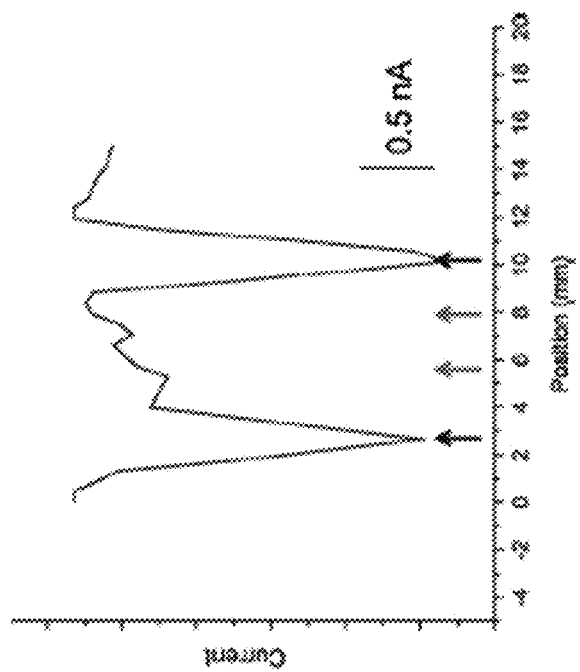
FIG. 6A is a graph of the electro catalytic signal recorded at a substrate pad modified with two strips of well-matched and two strips of mismatched DNA as disclosed herein, in which the bulk of the electrochemical signal from the substrate pad shows a classic electrocatalytic peak, indicating the presence of some well-matched DNA on the electrode surface, according to embodiments of the present invention.

Attachment of DNA onto the mixed monolayer was confirmed by recording a cyclic voltammogram (CV) at the substrate pad in the presence of 200 µM ferricyanide and 2 µM methylene blue (MB) (FIGS. 5A, 5B). The CV displays a large, irreversible reduction at ~−0.4 V, characteristic of DNA-mediated electrocatalytic reduction of ferricyanide by methylene blue (FIG. 6A). (See, e.g., Kelley et al., *Nucl. Acids Res.* 1999, 27, 4830-4837 and Chaubey, A. S.; Malhotra, B. D. *Biosensors and Bioelectronics* 2002, 17, 441-456, the entire contents of both of which are herein incorporated by reference.)

Although this experiment confirms that DNA is present on the surface, it provides no information on either the homogeneity or the types of DNA present.

Figure 6B:
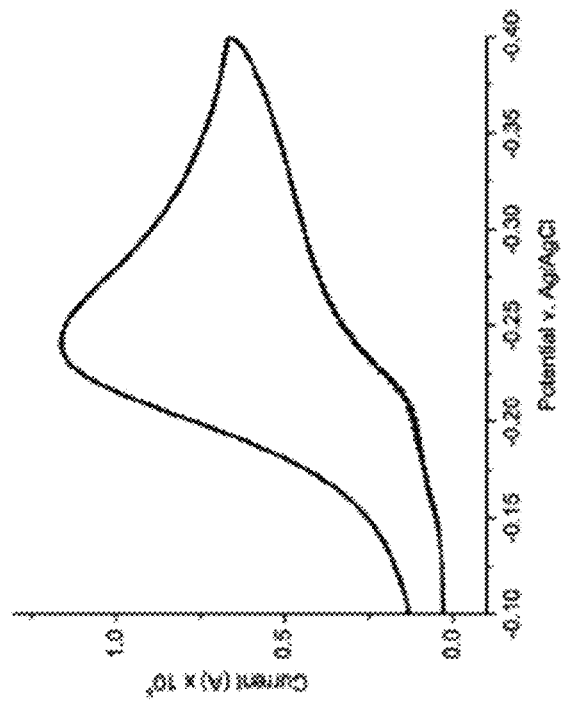
FIG. 6B is a graph of the electrochemical response of the probe electrode as a function of its position over the same substrate surface as in FIG. 6A using the two-electrode detection method in which the matched DNA (black arrows) and mismatched DNA (red arrows) are detected, according to embodiments of the present invention.

Indeed, the bulk response shown in FIG. 6B was obtained from a surface patterned with two strips of well-matched DNA and two strips of DNA containing a single-base mismatch. To interrogate the substrate more closely, a 100-µm gold electrode positioned above the substrate electrode using an x,y,z-stage was employed as a secondary electrode to create a detection system that enables spatial resolution in the x-y plane, as described herein (Materials and Methods). DNA-mediated reduction of ferricyanide (via methylene blue electrocatalysis) occurs only at locations on the substrate electrode addressed with well-matched DNA. As a consequence, amperometric detection of ferrocyanide at the probe electrode signals the presence of intact DNA duplexes at proximal locations on the underlying pad. As shown in FIG. 6B, only Watson-Crick paired DNA (black arrows) is detected using this method; and sequences containing a mismatch (red arrows) yield no signals, owing to the attenuation of DNA CT by a disruption in the π-stack, as described in Gorodetsky, A. A. et al., *Bioconj. Chem.* 2008, 19, 2285-2296, and Muren, N. B. et al., *Phys. Chem. Chem. Phys.* 2012, 14, 13754-13771, the entire contents of both of which are herein incorporated by reference.

Figure 7:
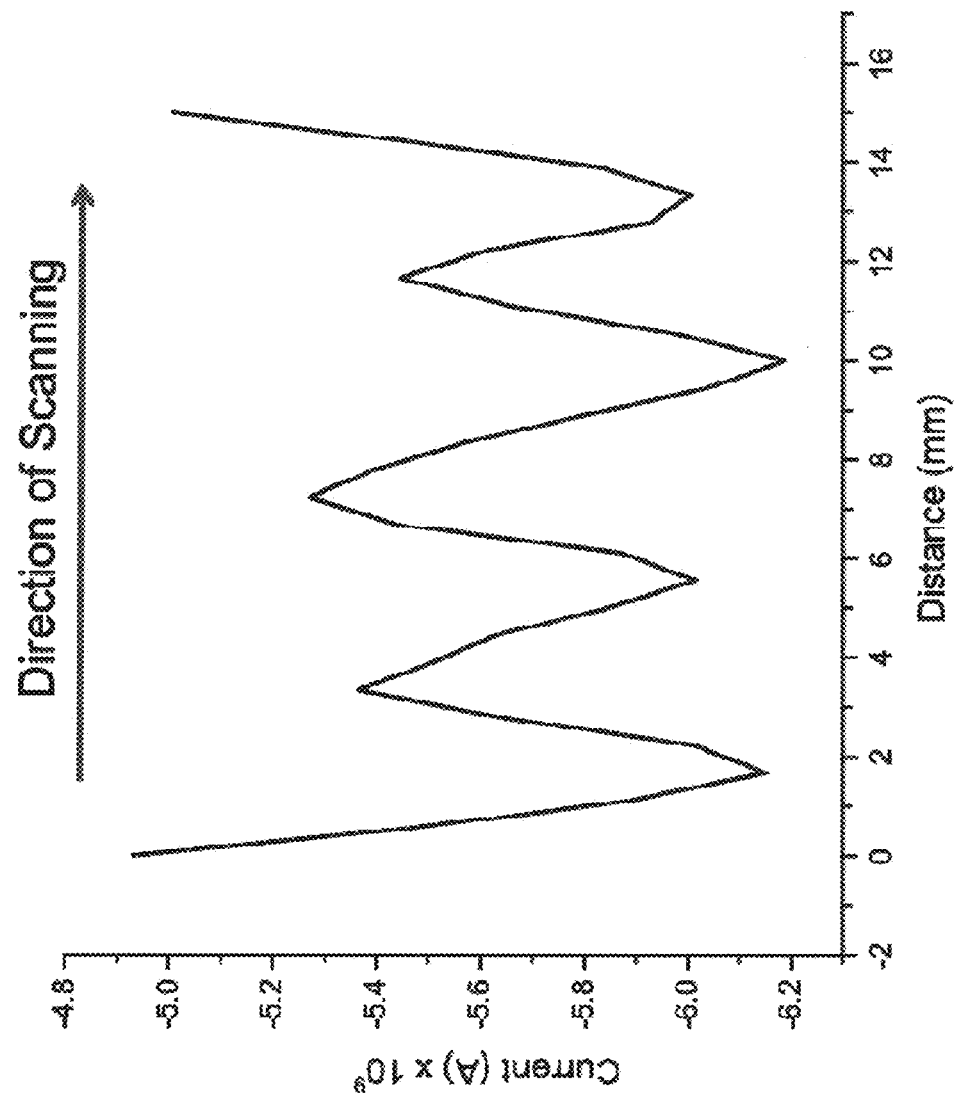
FIG. 7 shows a left to right scan (as indicated by the blue arrow) of a substrate electrode containing four strips of well-matched DNA in which the scan was measured in 2 µM methylene blue and 200 µM ferricyanide in Tris buffer (pH 7.6), according to embodiments of the present invention.

In this way, measuring ferrocyanide oxidation at the microelectrode tip as a function of position on the surface allows for spatial differentiation between the passivating layer and regions containing DNA on the substrate. Moreover, the utilization of a separate top probe electrode ensures that the current flow is DNA-mediated and amplified through electrocatalysis. Notably, this method provides reproducible current outputs for multiple strips of a single DNA sequence (FIG. 7), demonstrating a high level of reproducibility; the standard deviation for peak currents of DNA of the same sequence is 95 pA, or 1.5%. It should be noted that the full width half max of the DNA peaks is ~1 mm, the width of the patterning electrodes, indicating minimal diffusive spreading of the catalyst upon activation. (The peak width depends on the speed of scanning, which was optimal at ~0.6 mm/sec. Some inconsistencies are observed because the scanning was performed manually.)

Protein binding was also tested on this DNA platform using the eukaryotic transcription factor II D (TFIID) TATA binding protein (TBP) Nikolov, D. B. et al., *Nature* 1992, 360, 40-, the entire contents of which are herein incorporated by reference.

Figure 8B:
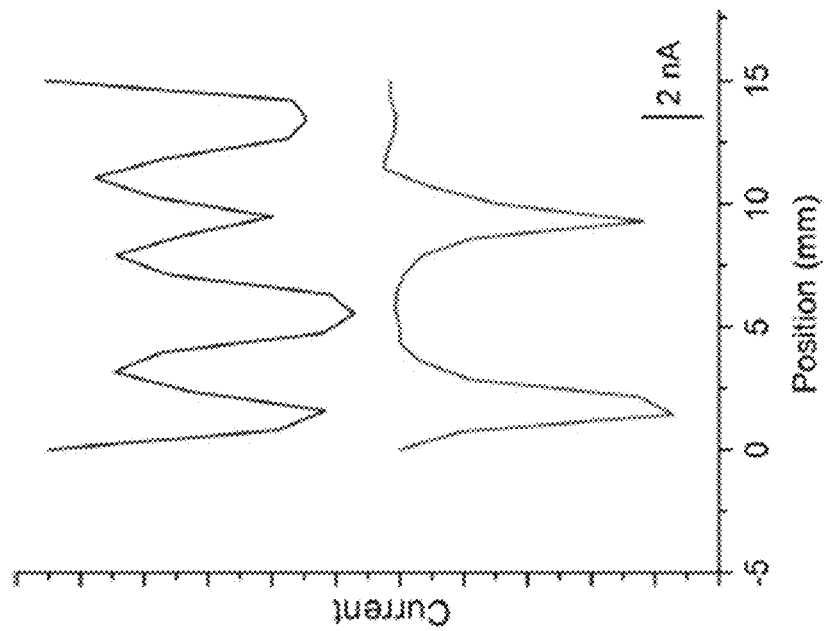
FIG. 8B is a distance versus current plot of the substrate electrode in which the current increases negatively down the y-axis; the blue trace is a scan in 2 µM methylene blue and 200 µM ferricyanide before the addition of TBP and after a 30-minute incubation in 100 µM BSA control; the red trace is a scan after a 15 minute incubation with 15 nM TBP protein in which the current corresponding to the TBP-binding sequences is diminished, while the current at locations without the protein binding site were unaffected, according to embodiments of the present invention.
Figure 8A:
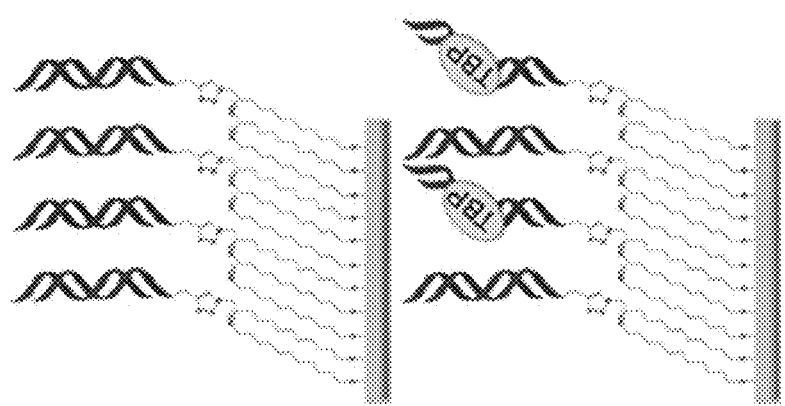
FIG. 8A is a schematic showing TATA binding protein (TBP) detection on a substrate surface patterned with four alternating strips of DNA with (red DNA) or without (blue DNA) a TBP binding site, according to embodiments of the present invention.

It was previously shown that TBP binding leads to attenuated CT in duplexes containing a TATA-binding sequence but does not affect duplexes lacking the binding site. (See, e.g., Gorodetsky, A. A et al., *J. Am. Chem. Soc.* 2008, 130, 2924-2925, and Boon, E. M. et al., *Nat. Biotechnol.* 2002, 20, 282-286, the entire contents of both of which are herein incorporated by reference. As such, alternating strips of TBP-binding sequences and non-binding sequences were patterned on a substrate surface, as described herein (Materials and Methods). As shown in FIGS. 8A, 8B, in the absence of TBP, four strips of well-matched DNA are detected. When TBP is titrated in, however, a loss of electrochemical signal occurs only at the location of the TBP sequences. At 15 nM, an almost complete signal loss is observed, indicating specific and sensitive protein detection with spatial resolution on this two-electrode platform.

Figure 9B:
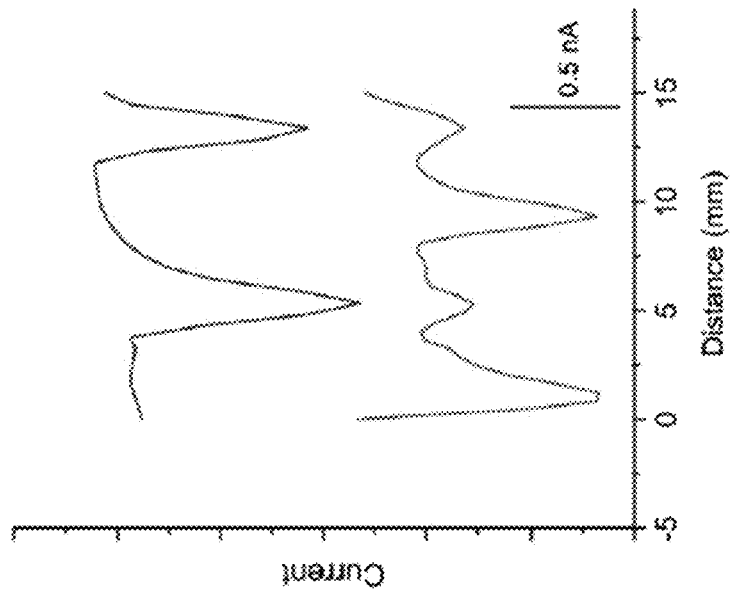
FIG. 9B is a distance versus current plot of the substrate electrode in which the blue trace is a preliminary scan in 2 µM methylene blue and 200 µM ferricyanide before hybridization; after the preliminary scan, the substrate surface was soaked in phosphate buffer (5 mM phosphate, 50 mM NaCl, pH 7) at 65° C. for 15 minutes; single stranded oligonucleotides that complement the formerly mismatched sequences were added and allowed to cool to room temperature for over 1 hour; the red trace is a scan of the post-rehybridization data in the which the mismatched sequences are now well matched and the formerly well-matched are now mismatched, according to embodiments of the present invention.
Figure 9A:
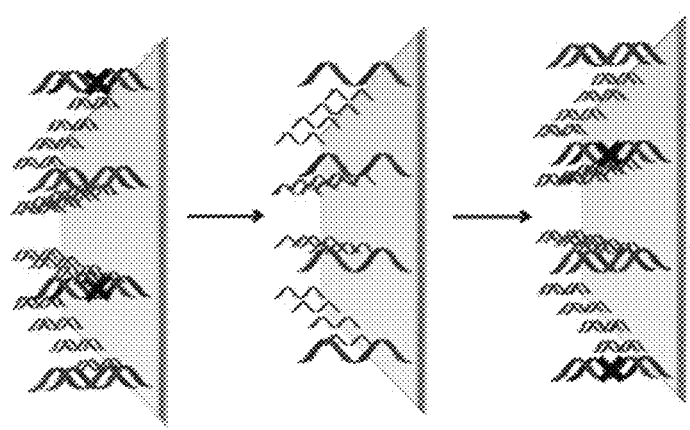
FIG. 9A is a schematic showing oligonucleotide detection through dehybridization and hybridization on a substrate surface patterned with two strips of well-matched DNA (two red helices) and two strips of mismatched DNA (one red helix and one blue helix), according to embodiments of the present invention.

A similar strategy was employed to detect selective DNA hybridization. Alternating strips of well-matched DNA and DNA containing a CA mismatch were patterned onto the electrode surface. Imaging the substrate from the top of the monolayer yields the expected pattern of alternating high and low currents at the probe tip (FIGS. 9A, 9B). The DNA on the electrode was then dehybridized by heating the substrate pad in 65° C. buffer for fifteen minutes. A strand of DNA fully complementary to the alkynyl strand that was originally mismatched was subsequently incubated on the surface for one hour, resulting in the formerly mismatched sequences being well-matched and vice-versa, as described herein (Materials and Methods). Rescanning the substrate electrode revealed almost complete reversal of signal locations, indicating that the majority of the DNA helices on the surface were dehybridized and rehybridized to an alternate complement. Our platform effectively differentiates between fully complementary duplexes versus those that contain single-base mismatches, making it ideally suited for assays based on hybridization. Because DNA CT-based assays rely on π-stacking interactions within fully annealed duplexes, they do not require stringent hybridization conditions.

Incorporating selective DNA patterning into a two-electrode platform thus enables sensitive detection of protein binding to DNA, as well as specific hybridization events with spatial resolution on a single surface. Multiple DNA probe sequences can be accurately grafted using readily available alkyne-labeled duplexes and an electrochemically-activated copper complex to initiate click coupling. DNA CT-based electrochemical assays are inherently more sensitive and selective than other DNA-based platforms, and as readout is accomplished at a secondary electrode, bulk surface defects that would otherwise complicate single-electrode measurements are readily detected. Moreover, detection at the secondary electrode insures that the signal is both DNA-mediated and electrocatalytically enhanced, yielding high differential sensitivity, indeed higher than that seen previously. The electrochemical DNA-grafting method of the present invention is well suited for preparing densely packed arrays of DNA sequences for use in multiple analyte detection on a single surface.

Materials and Methods.

Vapor Deposition. Gold evaporation was accomplished using aluminum masks and a CVC Metal Physical Vapor Deposition system. Glass slides were coated in MPS ([3-mercaptopropyl]-trimethoxysilane). Slides were cleaned by boiling at 70° C. for 10 minutes in Piranha solution (1:4 hydrogen peroxide: sulfuric acid), followed by baking for 10 minutes. Slides were then boiled in a 1:1:40 MPS: water: isopropyl alcohol solution for 10 minutes and then cured at 107° C. for 8 minutes. A 150 nm gold monolayer was formed on the slides with either the patterning or the substrate pattern using aluminum masks and a CVC Metal Physical Vapor Deposition system with 0.5 mm diameter gold wire, as described in Goss, C. A.; Charych, D. H.; Majda, M. *Anal. Chem.* 1991, 63, 85-88, the entire contents of which are herein incorporated by reference.

Duplex DNAs. Oligonucleotides were synthesized on an Applied Biosystems 3400 DNA synthesizer. Terminal C6 alkyne moieties were incorporated into the 5' end of one of the strands purchased from Glen Research. Complementary unmodified strands were also synthesized. Preparation of all of the oligonucleotides followed a reported protocol. Each oligonucleotide was purified by high-performance liquid chromatography (HPLC) using a gradient of acetonitrile and 50 mM ammonium acetate. Following purification, oligonucleotides were desalted by ethanol precipitation and quantified based on their extinction coefficients at 260 nm (IDT Oligo Analyzer). The following sequences were prepared: well matched: (SEQ ID NO: 1) 5'-CC—$(CH_2)_6$-GCT CAG TAC GAC GTC GA-3' with its unmodified complement, a mismatch-containing sequence with a CA mismatch at the $9^{th}$ base pair: (SEQ ID NO: 2) 5'-TCG ACG TCA TAC TGA GC-3', and a TBP-binding sequence: (SEQ ID NO: 3) 5'-CC—$(CH_2)_6$-GGC GTC TAT AAA GCG ATC GCG A-3' with its unmodified complement.

Cu(I) Activation. Degassed $[Cu(phendione)_2]^{2+}$ was used as the inert catalytic precursor because of its aqueous solubility. $[Cu(phendione)_2]^{2+}$ was prepared by combining 1,10-phenanthroline-5,6-dione (Sigma Aldrich) (294.3 mg, 1.4 mmol) with $CuSO_4$ (Sigma Aldrich) (111.7 mg, 700 μmol) in 5 mL of deionized water. ESI-MS: 580.2 (calc: 580.0). The complex was isolated as the $PF6^-$ salt or used directly in situ. Before application to the electrode surface, the complex was diluted to a final concentration of 50 μM in Tris buffer (10 mM Tris, 100 mM KCl, 2.5 mM $MgCl_2$, 1 mM $CaCl_2$, pH 7.6) and thoroughly degassed. When a sufficiently negative potential is applied to this compound, Cu(II) is reduced to Cu(I). A BAS Epsilon bipotentiostat was used both to apply potentials and record data. A constant potential was applied to the patterning electrodes that is sufficiently negative to continuously activate the copper at that location. For the constant applied potential, −250 mV was used, and application was allowed to proceed for 15 minutes. The 100 μM catalyst (20 μL) with 20 μL 50 μM DNA in Tris buffer was used to pattern each strip. Residual catalyst interaction with DNA was a concern, but no change in duplex melting temperatures in the presence of catalyst was observed. Neither protein binding nor hybridization was affected by catalyst.

Detection using a second (probe) electrode. The height of the probe electrode (z) was adjusted manually by lowering the electrode onto a 100-um teflon spacer placed on the corner of the substrate pad. No attempt was made to control for drift; while the measured currents were remarkably consistent for each substrate pad, the absolute signals varied somewhat from substrate to substrate. Electrochemical images of substrate surface (FIGS. 6B, 7, 8B, and 9B) are presented as scans from left to right. In all cases, the scanning origin is indicated by a distance of 0 on the x-axis, and the distance increases positively in the direction of scanning. Additionally, multiple scans can be obtained at different locations on the substrate pad. Variation in current between different locations on the substrate pad enabled calculation of standard deviation.

TATA Binding Protein. TATA-Binding Protein (TBP) was purchased from ProteinOne and stored at −80 C until use. MicroBiospin 6 columns (BioRad) were used to exchange the shipping buffer for Tris buffer (10 mM Tris, 100 mM KCl, 2.5 mM $MgCl_2$, 1 mM $CaCl_2$, pH 7.6). Prior to electrochemical measurements with TBP, electrodes were incubated with 1 μM Bovine serum albumin (BSA) for 30 min, followed by rinsing with Tris buffer. TBP was titrated onto the surface in a range of 1 μM to 25 μM protein, with each concentration allowed to incubate for 15 minutes prior to scanning.

After a preliminary scan of duplex DNA on the electrode surface, dehybridization was induced through the heating of the surface in phosphate buffer (5 mM phosphate, 50 mM NaCl, pH 7.0) to 65° C. for fifteen minutes. Subsequently, the surface was rinsed with 65° C. phosphate buffer (pH 7.0). The complementary strand (25 μL of 50 μM strand) was then added to the surface and incubated for an hour while the surface cooled to ambient temperature. The surface was subsequently scanned again.

Example 2

Detection of DNMT1 Methyltransferase. DNA methylation is a central epigenetic mechanism that powerfully influences gene expression in cells. A genomic pattern of methyl groups, covalently added to cytosine at predominantly 5'-CG-3' sites, is maintained by DNA methyltransferases. Although essential for many cellular processes, aberrant methylation is associated with cancer. In particular, abnormal activity of DNA methyltransferases can lead to hypermethylation, which can silence tumor suppressor genes and promote cancerous transformations. (See, e.g., Jones, P. A. & Laird, P. W. *Nat. Genet.* 21, 163-167 (1999); Baylin, S. B. *Science* 277, 1948-1949 (1997); Jones, P. A. & Baylin, S. B. *Nat. Rev. Genet.* 3, 415-428 (2002); and Heyn, H. & Esteller, M. *Nat. Rev. Genet.* 13, 679-692 (2012), the entire contents of all of which are herein incorporated by reference.)

The most abundant mammalian methyltransferase, and an important diagnostic target, is DNMT1, which preferentially methylates hemimethylated DNA using the cofactor S-adenosyl-L-methionine (SAM). Measurements of DNMT1 activity currently require [methyl $^3$H]-SAM to observe radioactive labeling of DNA. In some embodiments of the present invention, an electrochemical platform as disclosed herein is used to detect DNMT1 activity in crude lysates from both cultured human colorectal cancer cells (HCT116) and colorectal tissue samples. The platform is a multiplexed detection system that combines both low-density DNA monolayer patterning with detection from a secondary electrode using electrocatalytically amplified DNA charge transport chemistry. The low-density DNA monolayer promotes the access of DNMT1 even in highly congested lysate samples, while electrocatalytic signal amplification markedly increases sensitivity. Femtomoles of DNMT1 in cellular samples are rapidly detected without antibodies or radioactive labels. Moreover, colorectal tumor tissue was distinguished from healthy adjacent tissue through differences in DNMT1 activity, illustrating the effectiveness of using this two-electrode platform for clinical applications.

Figure 10A:
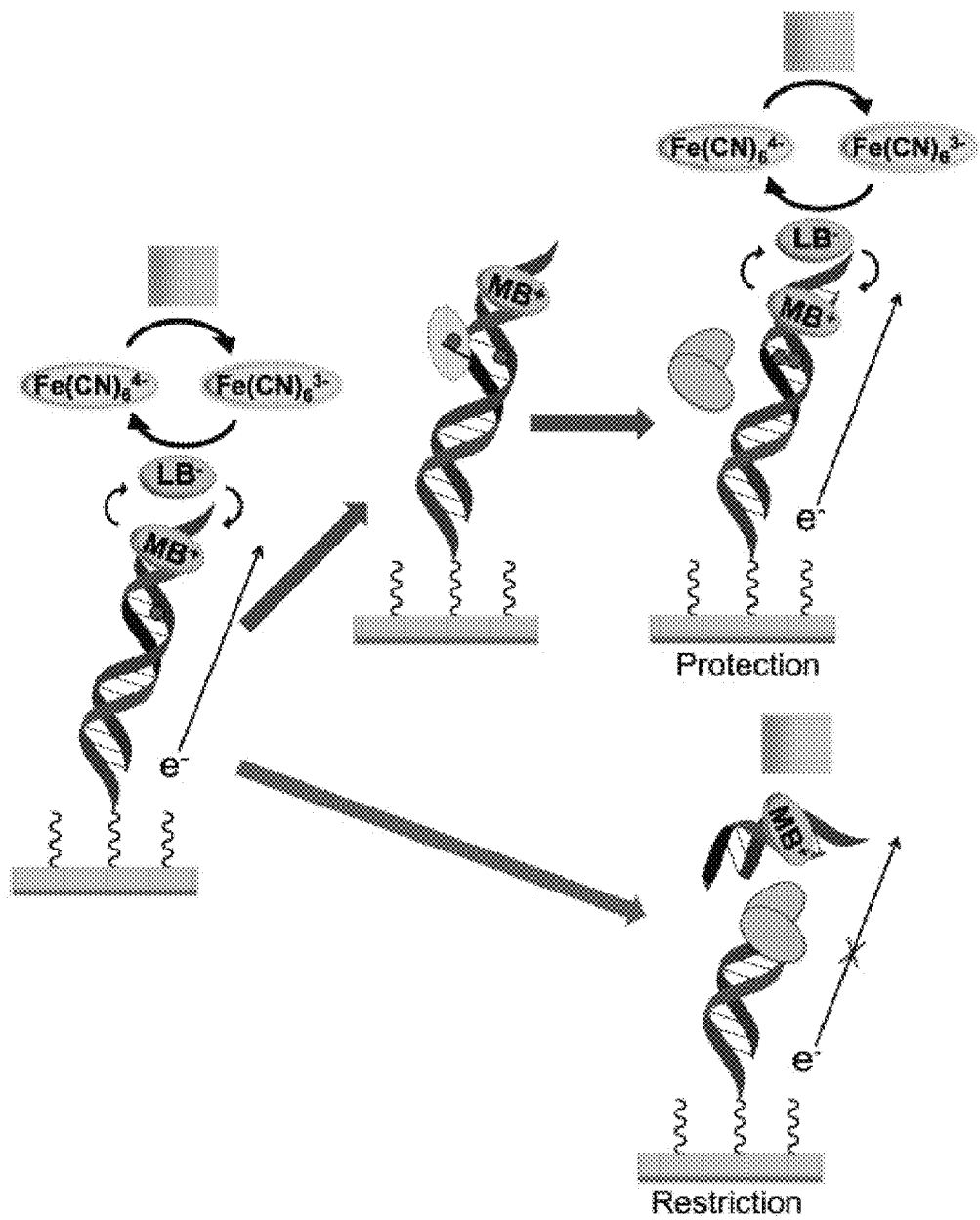
FIG. 10A is a schematic of the electrochemical detection of methylated DNA using the two-electrode platform in which methyltransferase (green) is added to the substrate electrode surface in a purified form or as a component of a lysate; the DNA on the substrate electrode is either methylated (indicated by green dot) by the protein to a fully methylated duplex (indicated by blue arrows) or is not methylated (indicated by red arrow); a methylation-sensitive restriction enzyme BssHII (purple) is then added, and if the DNA is fully methylated, the restriction enzyme will not cut the DNA and the electrochemical signal remains protected; and if the DNA is cut by the restriction enzyme and dissociates, the signal is diminished significantly, according to embodiments of the present invention.
Figure 10B:
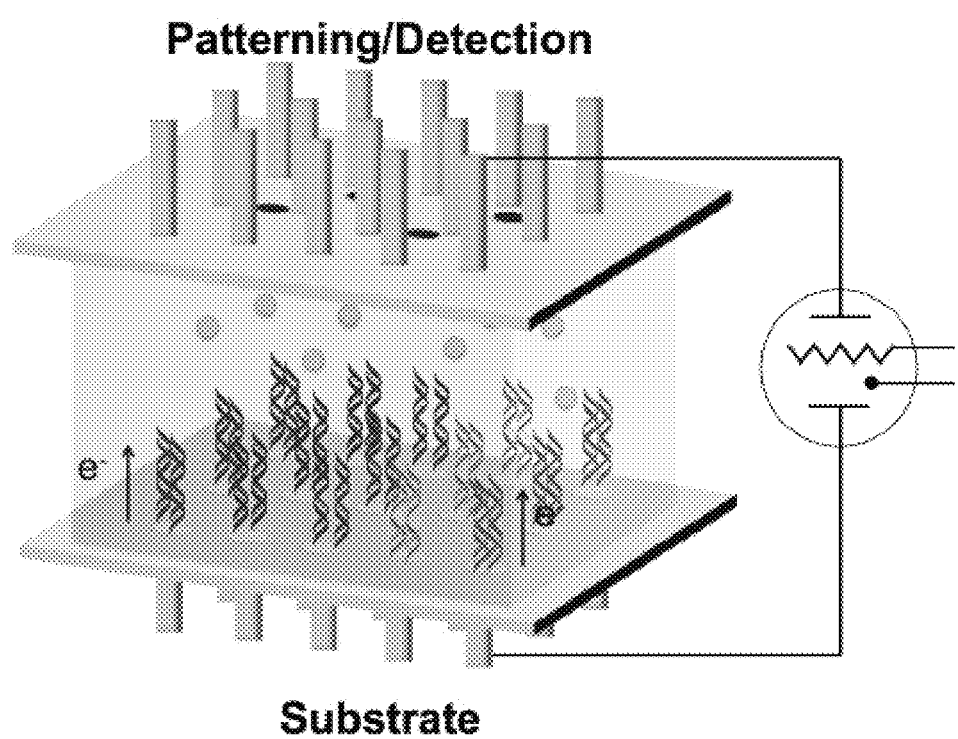
FIG. 10B is a schematic of an electrochemical detection platform having 15 electrodes (1 mm diameter each) in a 5×3 array, in which the DNA is added to the substrate electrode by an electrochemically-activated click reaction initiated by the patterning electrode of the different types of DNA represented by a different color (purple, blue, red, yellow, or green); and the electrocatalytic detection is performed by the secondary (detection) electrode, according to embodiments of the present invention.

As disclosed herein, the assay of the present invention includes a signal-on detection method for DNMT1 involving a methylation-sensitive restriction enzyme that converts the methylation state of the DNA into an electrochemical signal. If the DNA is fully methylated, the electrochemical signal remains 'on,' but if the DNA is unmethylated or hemimethylated, the restriction enzyme cleaves the DNA, significantly diminishing the electrochemical signal (FIGS. 10A, 10B). This platform uses electrocatalytic signal amplification involving a freely diffusing electrocatalyst (methylene blue), which eliminates the need for redox-labeled DNA.[26]

Electrochemical Platform. Using a 15-pin setup, low-density DNA monolayers were formed on one set of electrode surfaces by DNA patterning from a secondary electrode. First, thiol monolayers with 50% azide and 50% phosphate head groups were prepared on the gold pins. Subsequently, specific DNA sequences were tethered to individual pins using electrochemically-activated $Cu^{1+}$ click chemistry. The secondary electrode activates the inert copper catalyst precursor only at specific locations on the primary electrode surface. Multiple sequences of DNA with different methylation states in the restriction enzyme binding site were thereby patterned onto particular electrodes (FIG. 10B). As the platform is arranged in a 5×3 electrode array, five experimental conditions were run in triplicate for each experiment.

Figure 11A:
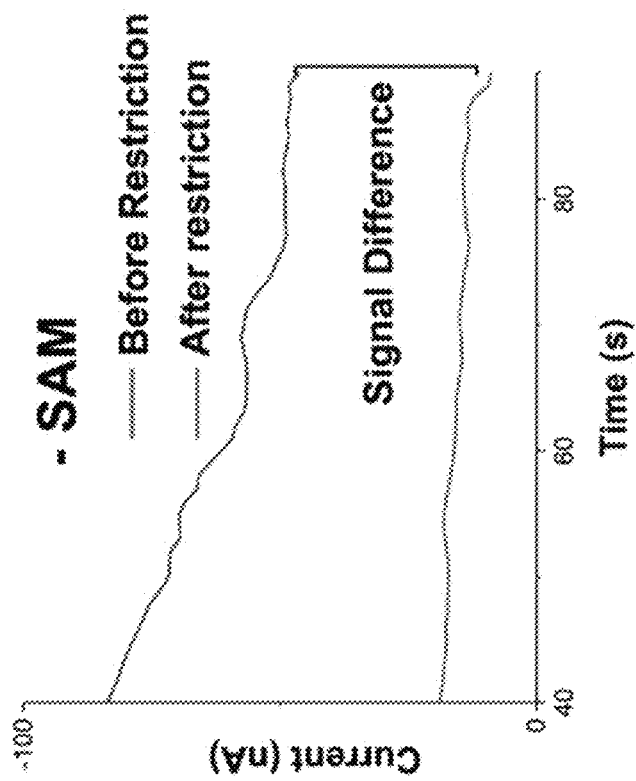
FIG. 11A is the raw data from a detection electrode in the presence of 160 µM S-adenosylmethionine (SAM) cofactor in which the blue trace is the first scan after the platform was treated with modified hemimethylated DNA and wild type lysate (source of DNMT1 methyltransferase) followed by treatment with 1 µM protease in phosphate buffer at 37° C., and the red trace is the scan after the platform is treated with 1500 units/mL BsshII for 1.5 hours at 37° C., according to embodiments of the present invention.
Figure 11B:
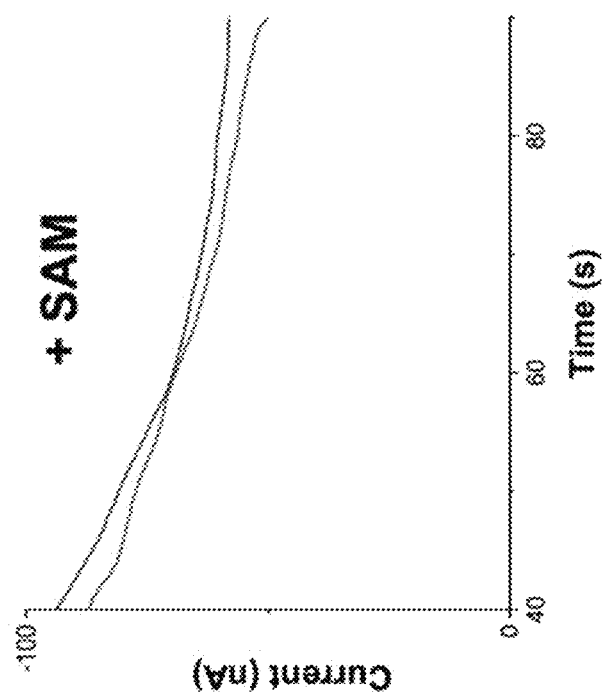
FIG. 11B is the raw data from a probe electrode in the absence of SAM cofactor in which the blue and red traces represent the same conditions as in FIG. 11A, according to embodiments of the present invention.
Figure 11C:
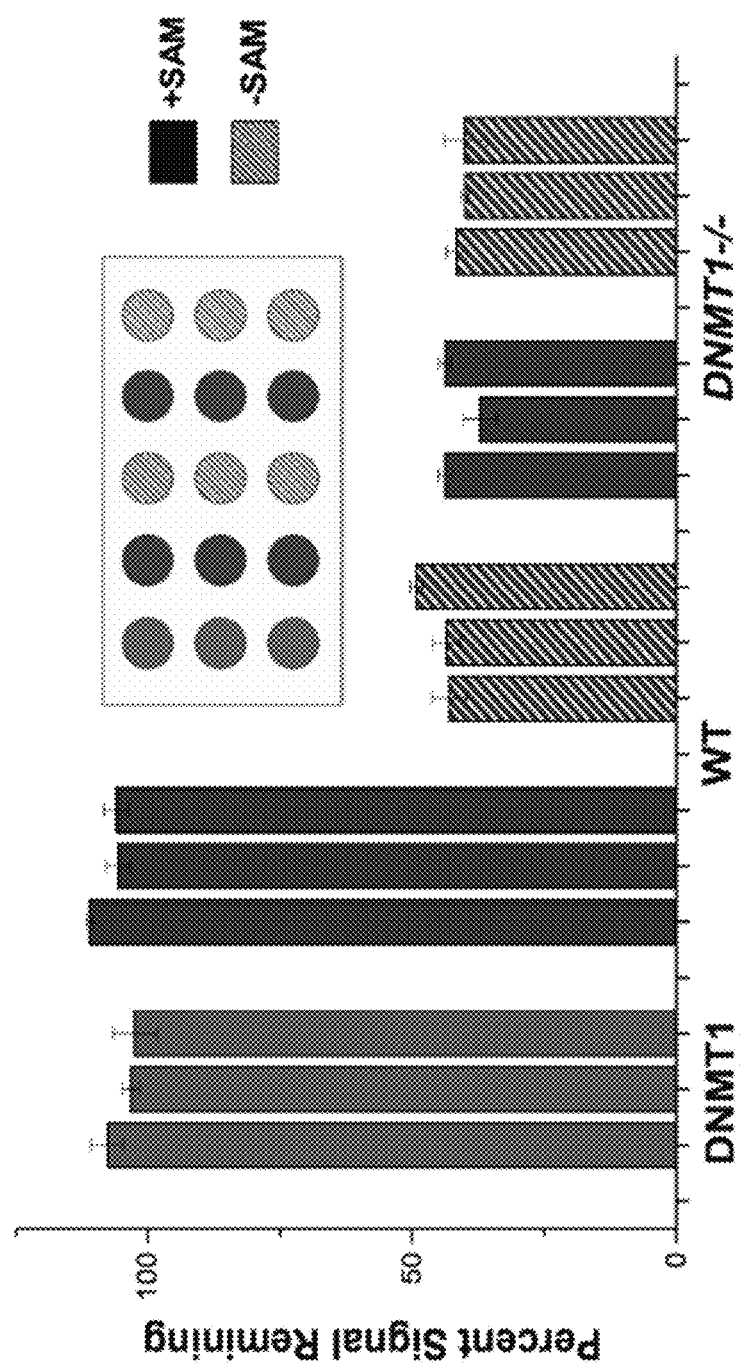
FIG. 11C is a graph of the percent of signal remaining after the indicated conditions including: the presence of purified DNMT1 protein (with SAM), wild type lysate (WT) with and without SAM; and DNMT1–/– lysate with and without SAM, in which the substrate surface and corresponding target substrate and reactants are indicated with corresponding colored wells (dots), which DNMT1 is green, WT is blue, and DNMT1–/– is red and with SAM is solid and without SAM is cross hatched, according to embodiments of the present invention.
Figure 12:
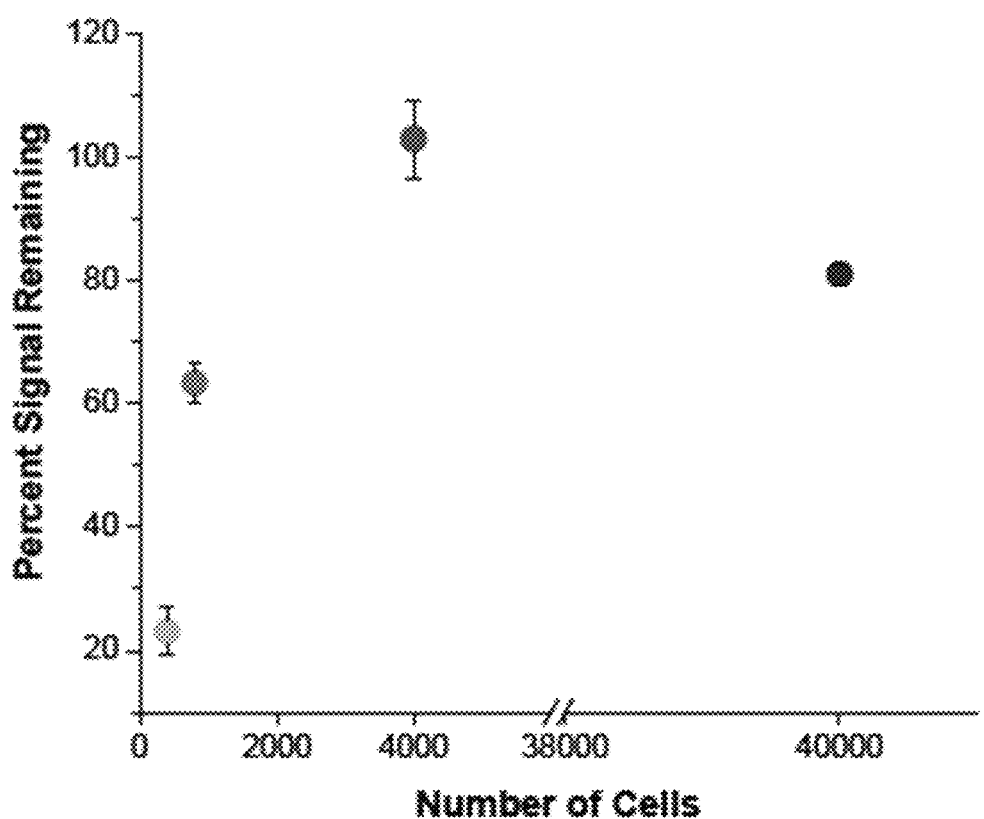
FIG. 12 is a graph showing the number cells in a cell lysate versus the electrode signal (in percent signal remaining) in order to optimize the concentration of a cell lysate to produce enough of a signal while not overloading the substrate surface, according to embodiments of the present invention.

Electrochemical measurements were obtained by constant potential amperometry over 90 seconds. Electrodes were measured after treatment with methyltransferase, either in its purified form or in lysate, and again after treatment with 1500 units/mL of the restriction enzyme BssHII. Lysate was prepared through a simple treatment (cell disruption and buffer exchange). FIGS. 11A, 11B, and 11C show the raw data collected for two individual electrodes treated with crude lysate, one in which the signal remains 'on' in the presence of the SAM cofactor and one in which the signal is turned 'off' in the absence of cofactor. Additionally, the reproducibility of the platform is shown (FIGS. 11A, 11B, 11C), with the 15 individual electrodes of a single assay. High concentrations of lysate were found to diminish the electrochemical signal, likely due to crowding on the DNA-modified electrode, limiting access and reaction of the methyltransferase. Multiple concentrations of lysate were tested (FIG. 12), but a concentration corresponding to 4,000 cells per electrode was dilute enough to allow access of DNMT1 to the DNA on the surface while still containing sufficient DNMT1 to produce measurable activity.

To further combat signal decreases caused by undesired DNA-binding proteins, after electrodes are treated with lysate, a protease treatment step is incorporated to remove remaining bound protein before the electrochemical measurements. Methyltransferase activity is then determined by the percent signal remaining after BssHII treatment. If the DNA is cut by the restriction enzyme, the signal is low, indicating little methyltransferase activity. It is noteworthy that the percent signal remaining is always non-zero because even after restriction, a DNA fragment remains that can generate an electrochemical response with the noncovalent methylene blue redox probe; electrochemical amplification is proportional to the amount of bound methylene blue, and therefore to DNA length.

Figure 13:
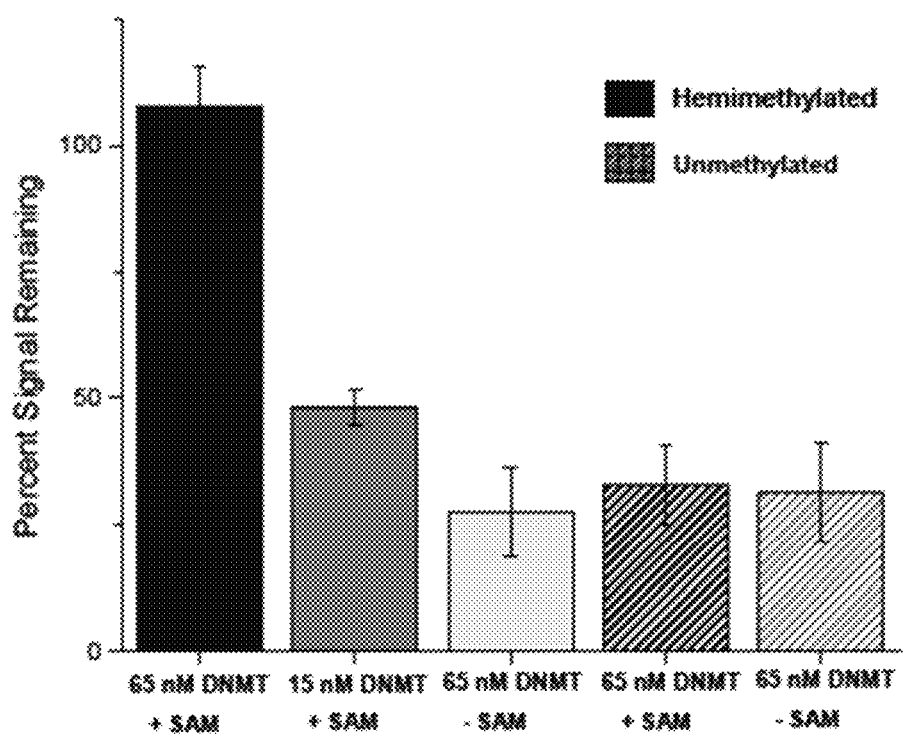
FIG. 13 is a graph showing the percent signal remaining after treatment with the indicated conditions, including: with purified DNMT1 in the presence and absence of SAM and with hemimethylated or unmethylated DNA, as indicated, according to embodiments of the present invention.

Purified DNMT1 was first used to establish the sensitivity and selectivity of this platform (FIG. 13) and was subsequently included alongside lysate activity measurements as a positive control. Full protection of the DNA-mediated signal is seen with 65 nM DNMT1 protein detected on a hemimethylated DNA substrate in the presence of the SAM cofactor, although protein is easily detectable at a 15 nM concentration with 48±3% signal protection. Without SAM, only 33±5% signal protection is observed. Similarly, little DNA protection (31±6% signal protection) is observed with the unmethylated substrate. This is explained by the strong preference of DNMT1, as a maintenance methyltransferase, for a hemimethylated substrate.

Figure 14C:
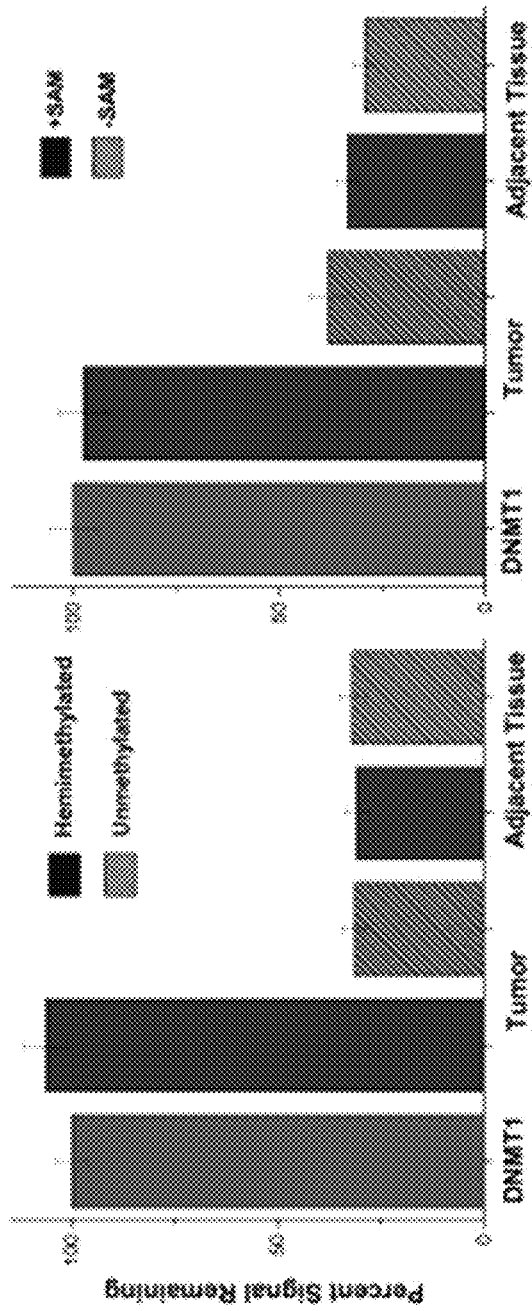
FIG. 14C is a graph showing the percent signal remaining on hemimethylated (solid) and unmethylated (cross hatched) DNA, as indicated, with tumor lysate (blue) and adjacent tissue lysate (red) compared to purified DNMT1 (green), according to embodiments of the present invention.
Figure 14D:
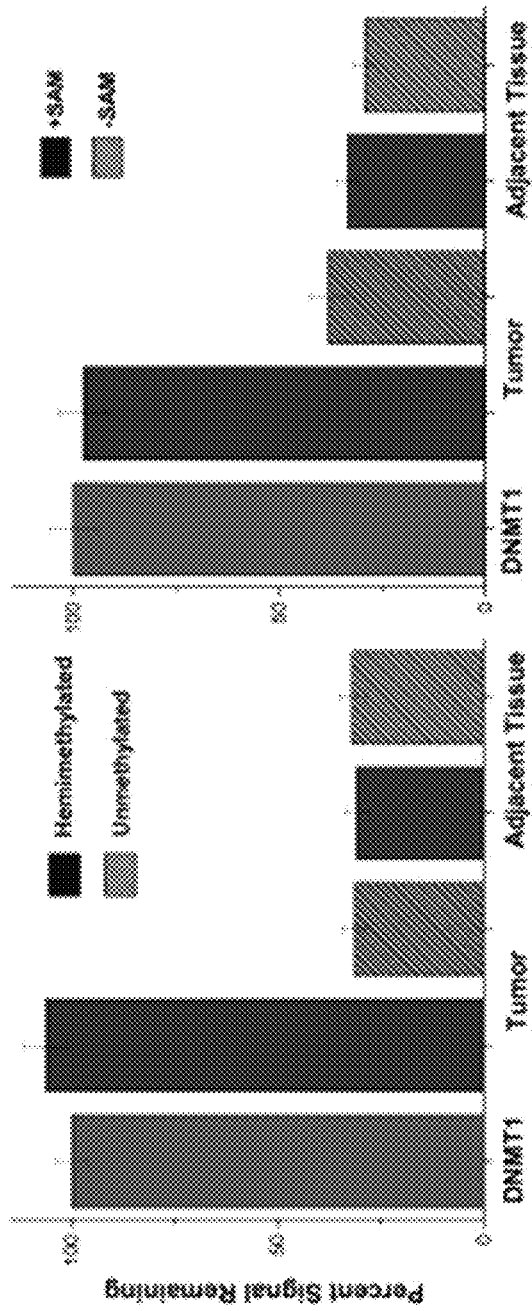
FIG. 14D is a graph showing the percent signal remaining in the presence of SAM (solid) or absence of SAM (cross hatched), as indicated, with tumor lysate (blue) and adjacent tissue lysate (red) compared to purified DNMT1 (green), according to embodiments of the present invention.

Differential Detection of DNMT1 Activity from Multiple Crude Cultured Cell Lysates. We then tested the ability of the platform to differentiate between lysate from a parent (HCT116 wild type) colorectal carcinoma cell line and a cell line that does not express DNMT1 (HCT116 DNMT1$^{-/-}$). Both the methylation state of the substrate and the presence of the cofactor SAM were tested for specific detection of DNMT1 activity (FIGS. 14A, 14B, 14C, 14D). The 'signal on' specificity for the hemimethylated DNA substrate indicates unambiguous DNMT1 activity (maintenance methylation), and not DNMT3a or DNMT3b activity (de novo methylation). Signal protection is dependent on the presence of DNMT1 (purified or from parent lysate) as well as the cofactor SAM (FIG. 14B) on the hemimethylated substrate (FIG. 14A). The remaining electrodes, treated either with parent lysate without SAM, or DNMT1$^{-/-}$ lysate independent of the cofactor, had significantly attenuated signals after restriction enzyme treatment.

Detection of DNMT1 Activity from Human Tumor Tissue.

Figure 15:
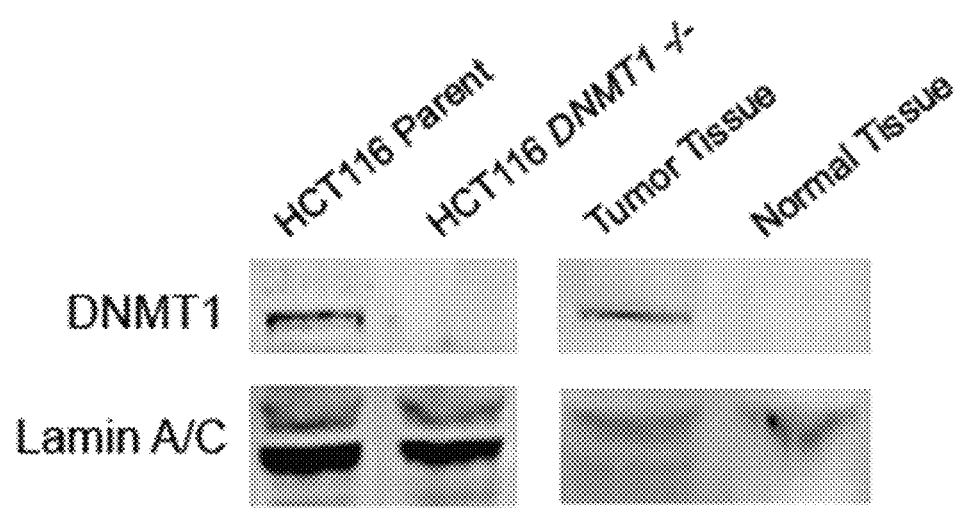
FIG. 15 is a Western blot of the wild type lysate (HCT116 parent), DNMT−/− lysate (HCT116 DNMT1−/−), tumor tissue lysate, and adjacent (normal) tissue lysate as indicated and used herein, with blotting of DNMT1 protein and Lamin A/C protein in the indicated lysates, according to embodiments of the present invention.

Human biopsy tissue samples were similarly evaluated, and tumor tissue was readily distinguished from adjacent normal tissue (FIGS. 14A, 14B, 14C, 14D). The optimal amount of tissue for detection from these samples was found to be approximately 500 μg per electrode; typical colon punch biopsies yield 350 mg of tissue. Samples of colorectal carcinoma tissue as well as the adjacent healthy tissue were prepared following the same protocol as described for the cultured cell lysate. The colorectal carcinoma tissue showed differential activity with our electrochemical platform. The tumor sample, which showed greater signal protection, was sensitive to both substrate and cofactor, consistent with high DNMT1 methyltransferase activity, similar to the parent colorectal carcinoma cells. In contrast, the normal tissue sample showed low methyltransferase activity, as seen through the minimal electrochemical signal protection (FIGS. 14A, 14B, 14C, 14D). These data clearly indicate that this tumor can be effectively differentiated from healthy tissue through electrochemical DNMT1 activity measurement. By western blot, the relative abundance of DNMT1 in the tumor tissue as compared to healthy tissue was quantitatively consistent with the electrochemical results (FIG. 15).

Figure 16:
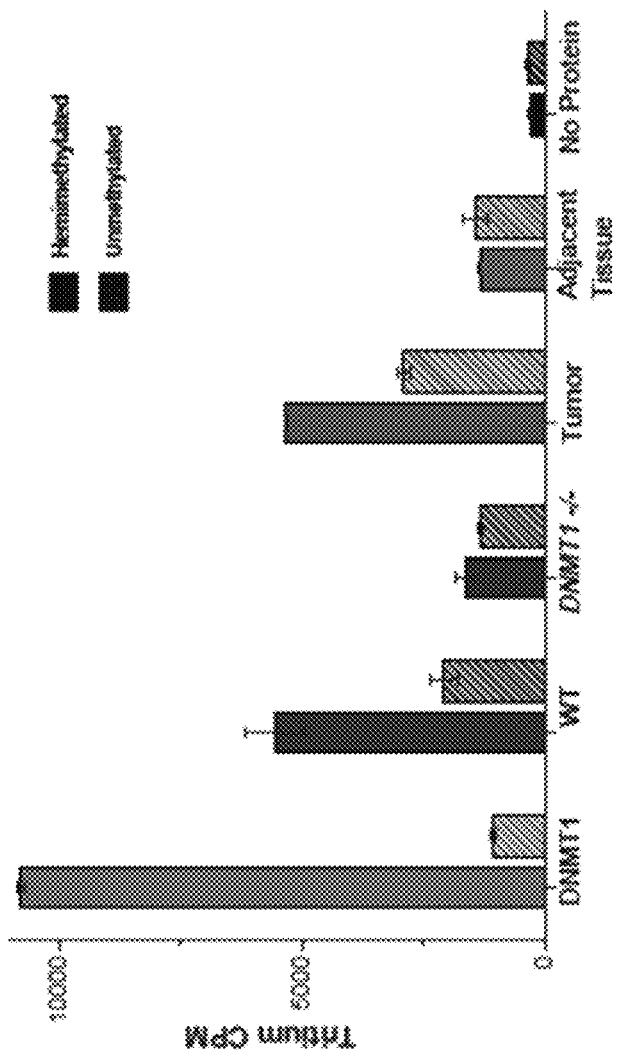
FIG. 16 is a graph showing the amount of tritium ($^3$H) in counts per minute (CPM) that is incorporated into hemimethylated (solid) or unmethylated (cross hatched) DNA after incubation with $^3$H-SAM and purified DNMT1 protein (green), wild type lysate (blue), DNMT1−/− lysate (maroon), tumor lysate (red), adjacent (normal) tissue lysate (blue), and no protein or lysate (black), according to embodiments of the present invention.

Lysate activities were also tested by a $^3$H-SAM assay, and relative activities of the various samples were comparable to those determined electrochemically (FIG. 16). However, as is typical for such radioactivity assays, activity measurements observed among trials of the $^3$H-SAM assay were extremely variable, much more so than with the electrochemical platform. Activity differences between the tumor and healthy tissue were seen only at concentrations of approximately 1 mg of tissue per sample, significantly higher than what is needed for electrochemical detection.

Implications.

DNMT1 is an important clinical diagnostic target due to its connection to aberrant genomic methylation, which is linked to tumorigenesis in cancer, including colorectal carcinomas. Direct detection of methylation activity from crude lysates provides an early method of cancer screening and can also inform treatment decisions. However, direct detection is challenging, as crude samples contain complex mixtures of biological material that clogs the apparatus and impedes detection of the activity of a specific protein. Furthermore, the detection platform must be sufficiently sensitive to analyze small clinical samples. The electrochemical assay for DNMT1 methylation activity according to embodiments of the present invention circumvents these problems. For example, patterning on the electrode avoids clogging of the platform. That is, patterning on the electrode tunes the separation of the DNA helices, thereby enabling the target DNA-binding proteins in the lysate to have ample access to the individual DNA helices on the surface. Additionally, the platform of the present invention is also sensitive and selective without the use of radioactivity through the combination of electrocatalytic signal amplification, low-density DNA monolayers and dilute lysate solutions. This sensitivity enables detection from both cultured colorectal cancer cells and tissue biopsy specimens. It is noted that substrate specificity was confirmed by detecting the maintenance methyltransferase DNMT1, and not the de novo methyltransferases DNMT3a or DNMT3b. Additionally, with the platform of the present invention, healthy tissue is easily distinguished from tumor tissue using very small amounts of sample, making this platform an important step toward effective clinical diagnostics for aberrant methylation.

While platforms exist for detection of particular biomolecules from cell lysate, they often sacrifice specificity or require significant sample purification prior to detection. The electrochemical platform of the present invention, in contrast, is capable of detection of human methyltransferase activity from crude lysate of both cultured cells and tissue samples. No difficult or time-consuming purification steps are necessary, and, for each electrode, only approximately 4000 cultured cells or approximately 500 μg tissue sample are required. DNMT1 activity measured from these lysates is both substrate-selective and dependent on the presence of SAM. No antibodies or substrate labeling are required. The ease of detection, small sample size required, and minimal lysate purification necessary make this electrochemical platform ideal for clinical applications.

Materials and Methods.

DNA Synthesis and Purification.

Oligonucleotides were either synthesized on an Applied Biosystems 3400 DNA synthesizer or purchased from IDT. The terminal C6 alkyne moiety that was incorporated into the 5' end of one of the strands was purchased from Glen Research. Complementary unmodified strands were purchased from IDT. DNA was deprotected and cleaved from solid support with ammonium hydroxide (60° C. for 12 h). DMT removal is achieved through treatment of oligonucleotides with 80% acetic acid in water for 20 minutes. Each oligonucleotide was purified by high-performance liquid chromatography (HPLC) using a gradient of acetonitrile and 50 mM ammonium acetate. Following purification, oligonucleotides were desalted by ethanol precipitation and quantified by ultraviolet-visible spectrophotometry based on their extinction coefficients at 260 nm (IDT Oligo Analyzer). Oligonucleotide masses were verified by matrix-assisted laser desorption (MALDI) mass spectrometry. DNA duplexes were formed by thermally annealing equimolar amounts of single-stranded oligonucleotides in deoxygenated phosphate buffer (5 mM phosphate, 50 mM NaCl, pH 7.0) at 90° C. for 5 minutes followed by slowly cooling to 25° C.

The following sequences were prepared as follows with the BssHII restriction site underlined:

Alkyne:
(SEQ ID NO: 4)
5'-C$_2$-(CH$_2$)$_6$-GA CTG AGT ACT GCG CGC ACT GAT AGC-3'

Complement:
(SEQ ID NO: 5)
5'-GCT ATC AGT GCG CGC AGT ACT CAG TC-3'

Methylated Complement:
(SEQ ID NO: 6)
5'-GCT ATC AGT GCG C$^m$GC AGT ACT CAG TC-3'

DNA Monolayer Formation.

The two-electrode array was constructed as disclosed herein. Gold surfaces were polished with 0.03 micron polish before monolayer assembly. Mixed monolayers were formed on one of the plates using an ethanolic solution of 1 M 12-azidododecane-1-thiol (C$_{12}$thiolazide) and 1 M 11-mercaptoundecylphosphoric acid (Sigma Aldrich). Surfaces were incubated in the thiol solution for 18-24 h, followed by rinsing with ethanol and phosphate buffer (5 mM phosphate, pH 7.0). The water soluble [Cu(phendione)$_2$]$^{2+}$ (phendione=1,10-phenanthroline-5,6-dione) was synthesized by mixing two equivalents of phendione with copper sulfate in water. Covalent attachment of DNA to mixed monolayers containing 50% azide head group and 50% phosphate head group through electrochemically-activated click chemistry was accomplished by applying a sufficiently negative potential to the secondary electrode. Specifically, a constant potential of −350 mV was applied to a secondary electrode for 25 minutes, allowing for precise attachment of the appropriate DNA to a primary electrode; 40 µL of 100 µM catalyst and 80 µL of 50 µM DNA in Tris buffer (10 mM Tris, 100 mM KCl, 2.5 mM MgCl$_2$, 1 mM CaCl$_2$, pH 7.6) were added to the platform for covalent attachment.

Cell Culture and Lysate Preparation.

HCT116 cells, either parent or DNMT1$^{-/-}$ (Vogelstein Lab), were grown in McCoy's 5A media containing 10% FBS, 100 units/mL penicillin and 100 µg/mL streptomycin, and were grown in tissue culture flasks (Corning Costar, Acton, Mass.) at 37° C. under a humidified atmosphere containing 5% CO$_2$.

Approximately 6 million cells were harvested from adherent cell culture by trypsinization, followed by washing with cold PBS and pelleting by centrifugation at 500 g for five minutes. An NE-PER nuclear extraction kit (Pierce from Thermo Scientific) was used to extract nuclear isolate, which was buffer exchanged by size exclusion spin column (10 kDa cutoff; Amicon) into DNMT1 activity buffer (50 mM Tris-HCl, 1 mM EDTA, 5% glycerol, pH 7.8). Cell lysate was immediately aliquoted and stored at −80° C. until use. A BCA assay (Pierce) was used to quantify the total amount of protein in the lysate. The total protein concentration at which the lysate was frozen was 35,000-50,000 µg/mL.

Tissue samples were obtained from CureLine. Colorectal carcinoma as well as healthy adjacent tissues were obtained. Approximately 150 mg of tissue were homogenized manually, followed by nuclear extraction, buffer exchange, storage and quantification as described above. The total protein concentration at which the lysate was frozen was 35,000-50,000 µg/mL.

DNMT1 expression was confirmed by Western blot. Samples were mixed with Laemmli reagent and betamercaptoethanol and probe sonicated for 10 seconds, followed by heat inactivation at 90° C. for 5 minutes. Samples were loaded onto 4-12% polyacrylamide gels in MOPS buffer and run at 175 mV for 1.5 hours. Gels were subsequently transferred to membranes with a dry transfer procedure for 1.5 h. Membranes were then blocked with 5% milk in Tris-buffered Saline with 0.1% Tween 20 (TBST, pH 7.6) at ambient temperature for 1 hour, followed by overnight incubation with a 1° antibody in milk and 3% BSA (w/v) (1:2000 for DNMT1 (New England Biolabs) and 1:1000 for Lamin A (Santa Cruz Biotechnology)) for either DNMT1 or Lamin A. The membranes were then rinsed with TBST buffer. Membranes were incubated with goat anti-rabbit 2° antibody (Abcam Incorporated) (1:7500 in 5% milk in TBST) for 1 hour and then rinsed with TBST, followed by scanning on an Odyssey infrared gel scanner. Resulting Western blots are shown in FIG. 15.

Electrochemistry.

All electrochemistry was performed on a bipotentiostat (BASinc.) with two working electrodes, a platinum wire auxiliary electrode and an AgCl/Ag reference electrode. All electrochemistry was performed as constant potential amperometry for 90 seconds with an applied potential of 320 mV to the secondary electrode and −400 mV to the primary electrode. All scans were performed in Tris buffer (10 mM Tris, 100 mM KCl, 2.5 mM MgCl$_2$, 1 mM CaCl$_2$, pH 7.6) with 4 µM methylene blue and 300 µM potassium ferricyanide. Scans were taken of each of the 15 secondary pin electrodes, and the reported variation in the data represents the standard error across three measurements of three electrodes, all at a given condition.

To incubate electrodes with desired proteins, a 1.5 mm deep Teflon spacer was clipped to the primary electrode surface. Each electrode is isolated in an individual well that holds 4 µL of solution. For methyltransferase activity detection, a standard three electrodes were incubated with 65 nM DNMT1 (BPS Biosciences) with 160 µM SAM (New England Biolabs) and 100 µg/mL BSA. For electrodes incubated with lysate, lysate was either directly combined with SAM to a final SAM concentration of 160 µM or the lysate was diluted in DNMT1 activity buffer to the desired total protein concentration and then combined with SAM to a final SAM concentration of 160 µM. For the tissue lysate, 50 µg/mL BSA was also added. Each electrode had the desired solution added to the well and incubated at 37° C. for 2 hours in a humidified container. The primary electrode array was then treated with 1 µM protease solution in phosphate buffer (5 mM phosphate, 50 mM NaCl, pH 7.0) for 1 hour. The surface was then thoroughly rinsed with phosphate buffer (5 mM phosphate, 50 mM NaCl, pH 7.0) and scanned. The electrodes were subsequently incubated with the restriction enzyme BssHII at a concentration of 1500 units/mL for 1.5 h at 37° C. in a humidified container. BssHII was exchanged into DNMT1 activity buffer by size exclusion column (10 kDa, Amicon). The electrodes were again rinsed with phosphate buffer and scanned.

$^3$H-SAM Methyltransferase Activity Assay.

Methyltransferase activity was additionally tested using the conventional method of a $^3$H-SAM incorporation activity assay. The activity assay was performed as described in Pradhan, S. et al., *J. Biol. Chem.* 274, 33002-33010 (1999), the entire contents of which are herein incorporated by reference. In brief, 20 µL total reaction volumes were used for the $^3$H-SAM activity assay. DNA (20 µM), identical to that used as a substrate for the electrochemical assay including the hexynyl terminus, was used. $^3$H-SAM (0.5 µCi, Perkin Elmer) was added, and the reactions were carried out in DNMT1 activity buffer. BSA (100 μg/mL) was included for the purified DNMT1 reaction, which was used as a positive standard, along with a negative standard that contained no protein. For the lysate samples, lysate (~2 μL) was included in the reaction mixture, bringing the total protein content for the reaction mixture to 3500 μg/mL. Reactions were incubated at 37° C. for 2 hours and quenched with 30 μL of 10% TCA in water. The resulting solutions were spotted onto DE81 filter paper (Whatman) and air-dried for 15 minutes. Filter papers were then individually soaked in 10 mL of 50 mM Na$_2$HPO$_4$ for 15 minutes and rinsed with both 50 mM Na$_2$HPO$_4$ and 95% ethanol. Filter papers were then heated to 37° C. to dry for 15 minutes before liquid scintillation counting, using control samples in parallel for consistency.

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. A two-electrode detection system comprising more than one type of target substrate selected from the group consisting of a nucleic acid, a protein, and/or a small molecule, the detection system further comprising:
 (1) a substrate surface comprising a single working substrate electrode, wherein the single working substrate electrode comprises gold or carbon;
 (2) a substrate surface linker comprising mixed monolayers self-assembled onto the working substrate electrodes, such that the substrate surface linker comprises;
  (a) a first moiety attached to a plurality of positions on the substrate surface, wherein the first moiety comprises a thiol or diazonium salt that attaches to the substrate surface; and
  (b) more than one second attachment moiety and at least one second passivating moiety, the more than one second attachment moiety being reactive and capable of attaching to a single type of target substrate of the more than one type of target substrate and the at least one passivating moiety being unreactive;
   (i) wherein the more than one second attachment moiety of the substrate surface linker comprises an azide or an alkyne,
   (ii) wherein each of the more than one type of target substrate comprises a target linker moiety, the target linker moiety of each of the more than one type of target substrate comprises an azide or an alkyne that covalently binds to a corresponding azide or alkyne of the more than one second attachment moiety, and
   (iii) wherein the at least one second passivating moiety comprises a passivating compound;
 (3) an inactive copper catalyst precursor;
 (4) a patterning electrode pad in an interdigitated pattern of lines comprising more than one working probe electrodes;
  (i) wherein the more than one working probe electrodes are individually addressable and interspersed with at least one reference electrodes,
  (ii) wherein each of the one or more working probe electrodes corresponds to a different one of the more than one type of target substrate, and
  (iii) wherein each of the more than one working probe electrodes is positioned facing a different selected position of the plurality of positions on the substrate surface of the working substrate electrode, such that each of the at least more than one working probe electrodes is capable of applying a negative potential at its corresponding selected position on the substrate surface to activate the inactive copper catalyst precursor by electrochemical reduction of the inactive copper catalyst precursor at specific working probe electrodes on the patterning pad; and
 (5) a plurality of more than one type of target substrate spatially patterned and isolated by covalent bond to selected positions of the second attachment moiety of the substrate surface via a catalyst azide/alkyne coupling.

2. The detection system of claim 1, wherein:
 the inactive catalyst precursor comprises copper (II).

3. The detection system of claim 1, wherein the more than one second attachment moiety of the substrate surface linker and/or the linker moiety of at least one of the more than one type of target substrate is selected the group consisting of a 6-carbon azide, a 9-carbon azide, and a 12-carbon azide.

4. The detection system of claim 2, wherein the inactive catalyst precursor comprises copper(II)(bathophen)$_2$ and/or copper(II)(phendione)$_2$.

5. The detection system of claim 1, wherein the at least one second passivating moiety is selected from the group consisting of alkanes, alcohols, carboxylic acids, phosphates, and combinations thereof.

6. The detection system of claim 1, wherein the passivating compound is selected from the group consisting of mercaptoethanol, mercaptohexanol, mercaptoundecanol, mercaptohexane, mercaptohexanoic acid, mercaptoundecanoic acid, mercaptoundecylphosphoric acid, and combinations thereof.

7. The detection system of claim 1, wherein the amount of the more than one second attachment moiety of the substrate surface linker relative to the amount of the at least one second passivating moiety is 1% to 20%.

8. The detection system of claim 1, wherein at least one of the more than one type of target substrate comprises DNA and reactants that are selected to undergo a redox reaction, wherein the reactants comprise methylene blue and ferricyanide, such that the redox reaction comprises reduction of the ferricyanide.

9. The detection system of claim 1, The detection system of claim 1, wherein at least one of the more than one type of target substrate is hemoglobin, and wherein hemoglobin is selected to undergo a redox reaction, the redox reaction being a dioxygen reaction.

10. The detection system of claim 1, further comprising an analyte sample.

11. The detection system of claim 10, wherein the analyte sample is selected from the group consisting of nucleic acids, proteins, small molecules, cell suspensions, and cell lysates.

12. The detection system of claim 1, wherein the substrate surface comprises a flat surface or a hollow cylinder.

13. The detection system of claim 1, wherein the substrate surface is a hollow cylinder and each of the more than one working probe electrodes of the patterning electrode pad has a rod shape.

* * * * *

UNITED STATES PATENT AND TRADEMARK OFFICE
CERTIFICATE OF CORRECTION

PATENT NO. : 10,316,354 B2  
APPLICATION NO. : 14/331221  
DATED : June 11, 2019  
INVENTOR(S) : Ariel L. Furst et al.

Page 1 of 1

It is certified that error appears in the above-identified patent and that said Letters Patent is hereby corrected as shown below:

On the Title Page

In Column 2, item [56], Line 46      delete "Tian-" and insert -- Jian- --

In the Claims

In Column 22, Line 49 (approx.), Claim 9      after "claim 1,", delete "The detection system of claim 1,"

Signed and Sealed this  
Twenty-seventh Day of October, 2020

Andrei Iancu  
*Director of the United States Patent and Trademark Office*